United States Patent
Günay et al.

(10) Patent No.: US 12,239,816 B2
(45) Date of Patent: Mar. 4, 2025

(54) DRUG DELIVERY DEVICE CASSETTE

(71) Applicant: Eli Lilly and Company, Indianapolis, IN (US)

(72) Inventors: Murat Günay, Carmel, IN (US); Jared Alden Judson, Medford, MA (US); Russell Wayne Perkins, Carmel, IN (US); Anthony Lawrence Schaff, Carmel, IN (US)

(73) Assignee: ELI LILLY AND COMPANY, Indianapolis, IN (US)

( * ) Notice: Subject to any disclaimer, the term of this patent is extended or adjusted under 35 U.S.C. 154(b) by 0 days.

(21) Appl. No.: 18/246,631

(22) PCT Filed: Aug. 19, 2022

(86) PCT No.: PCT/US2022/040867
§ 371 (c)(1),
(2) Date: Mar. 24, 2023

(87) PCT Pub. No.: WO2023/023314
PCT Pub. Date: Feb. 23, 2023

(65) Prior Publication Data
US 2023/0256159 A1    Aug. 17, 2023

Related U.S. Application Data

(60) Provisional application No. 63/260,454, filed on Aug. 20, 2021.

(51) Int. Cl.
*A61M 5/14*       (2006.01)
*A61M 5/142*      (2006.01)
*A61M 5/315*      (2006.01)

(52) U.S. Cl.
CPC ...... *A61M 5/1413* (2013.01); *A61M 5/14244* (2013.01); *A61M 5/31576* (2013.01); *A61M 2005/14268* (2013.01); *A61M 2005/31588* (2013.01)

(58) Field of Classification Search
CPC .. A61M 2005/004; A61M 2005/14268; A61M 5/14248; A61M 5/14244;
(Continued)

(56) References Cited

U.S. PATENT DOCUMENTS 7,569,050 B2 * 8/2009 Moberg ............... A61M 5/1413
                                                    604/890.1
9,597,452 B2 * 3/2017 Henderson ............... A61M 5/24
(Continued)

FOREIGN PATENT DOCUMENTS

WO    2017165154    9/2017
WO    2019112886    6/2019
(Continued)

OTHER PUBLICATIONS

Patent Cooperation Treaty International Search Report of the International Searching Authority pertaining to International Application No. PCT/US2022/040867; International Filing Date: Aug. 19, 2022; Date of Mailing: Feb. 13, 2023.
(Continued)

*Primary Examiner* — Quynh-Nhu H. Vu
(74) *Attorney, Agent, or Firm* — M. Daniel Spillman

(57) ABSTRACT

A drug delivery device may include a cassette with a needle assembly and a cartridge. The cassette is configured to couple and decouple from a reusable module. The device may also comprise an orientation mechanism to orient the cassette in relation to another device, such as a reusable housing. The device may comprise an extendable and retractable needle assembly. The cassette configuration is adapted to have a stopper with a short travel (no more than 14 mm) to deliver 1 mL of medication. The cassette may have a ratio of height to diameter from 2:1 to 1:1. The cassette may include a pair of drivable interfaces for being driven to actuate the stopper to expel medication and to drive
(Continued)

the needle assembly between a retracted and extended configuration for controlled fluid communication between the needle and reservoir.

16 Claims, 28 Drawing Sheets

(58) Field of Classification Search
CPC .......... A61M 2005/14252; A61M 2005/2474; A61M 2005/31588; A61M 2205/6045; A61M 5/1413; A61M 2205/6054; A61M 5/31576; A61M 5/482
See application file for complete search history.

(56) References Cited

U.S. PATENT DOCUMENTS

| | | | |
|---|---|---|---|
| 2010/0007501 A1* | 1/2010 | Yang | B01L 3/5453 340/572.8 |
| 2011/0118694 A1 | 5/2011 | Yodfat et al. | |
| 2018/0085517 A1* | 3/2018 | Laurence | A61M 5/145 |
| 2019/0209773 A1* | 7/2019 | Shor | A61M 5/31528 |

FOREIGN PATENT DOCUMENTS

| | | |
|---|---|---|
| WO | 2021003409 | 1/2021 |
| WO | 2021050380 | 3/2021 |
| WO | 2022132675 | 6/2022 |
| WO | 2022132677 | 6/2022 |

OTHER PUBLICATIONS

Patent Cooperation Treaty Written Opinion of the International Searching Authority pertaining to International Application No. PCT/US2022/040867; International Filing Date: Aug. 19, 2022; Date of Mailing: Feb. 13, 2023.

* cited by examiner

DRUG DELIVERY DEVICE CASSETTE

FIELD OF THE DISCLOSURE

The present disclosure relates to a drug delivery device with a cassette. The cassette may comprise an extendable needle assembly.

BACKGROUND OF THE DISCLOSURE

Conventional injection devices are often used to drive a needle through a surface, for example in the injection of a drug, removing a fluid from a sealed container such as a vial, sampling within chemical instrumentation, and so on. Considering the example of injecting a patient with a drug, it is sometimes advantageous for the drug to be administered without the presence of a medical professional (e.g. when taken frequently). The use of standard glass cartridges may provide a challenge for developing a space-efficient injection device. Furthermore, the disposal of glass cartridges may incur more environmental costs when compared to other materials. Additionally, it may be a challenge to ensure that the injection device is properly assembled and oriented by a user before use.

SUMMARY

The present disclosure provides devices and methods for delivery of a medication comprising a cassette with a cartridge configured to retain a volume of a medication, and an extendable and retractable needle assembly.

According to an exemplary embodiment of the present disclosure, a drug delivery device includes a cassette that includes a cartridge configured to retain a volume of a medication; a stopper driving system configured to drive the medication from the cartridge, the stopper driving system including a stopper, wherein the stopper travels less than 10 mm to deliver a 1 mL volume of the medication; and a needle assembly directly coupled to the cartridge movable between an extended configuration and a retracted configuration, the needle assembly having an actuating gear movable between first and second positions, wherein in the extended configuration the actuating gear is in the second position and the needle assembly provides fluid communication between the cartridge and the needle assembly, wherein in the retracted configuration the actuating gear is in the first position and no fluid communication is provided between the cartridge and the needle assembly.

According to another embodiment of the present disclosure, a method of delivering a medication to a patient includes coupling a housing of a drug delivery device to a cassette; orienting the housing relative to the cassette; positioning the drug delivery device against a skin of the patient; actuating a needle assembly of the drug delivery device to extend a first needle into the skin of the patient and a second needle into a septum of a polymeric cartridge containing a volume of a medication; actuating a driving system to drive the medication from the polymeric cartridge through the needle assembly and to the patient; and retracting the first and second needles within the needle assembly.

According to another embodiment of the present disclosure, a drug delivery device includes a reusable housing; a cassette coupled to the reusable housing, wherein the cassette has a ratio of height to diameter from 2:1 to 1:1; a cartridge supported by cassette and configured to retain a volume of a medication; and an orientation mechanism configured to orient the cassette relative to the reusable housing.

According to another embodiment, a drug delivery device having a cassette to couple to a reusable module is disclosed. The cassette includes a cartridge configured to retain a volume of a medication. The cartridge extends between a proximal end and a distal end along an axis that is centrally located. A stopper driving system is configured to drive the medication from the cartridge. The stopper driving system includes a stopper and an interfacing end coupled to the stopper and configured to be driven by a first motor or actuating device of the reusable module to move the stopper. A needle assembly is directly coupled to the cartridge movable between an extended configuration and a retracted configuration. The needle assembly has an actuating gear movable between first and second positions. The actuating gear is configured to be directly or indirectly driven by a second motor or actuating device of the reusable module. In the extended configuration, the actuating gear is in the second position and the needle assembly provides fluid communication between the cartridge and the needle assembly. In the retracted configuration, the actuating gear is in the first position and no fluid communication is provided between the cartridge and the needle assembly. The interfacing end extends from an upper end of the cartridge and coaxial with the axis, and the actuating gear is disposed to be engaged externally by the second motor or actuating device of the reusable module at a location offset from the axis.

BRIEF DESCRIPTION OF THE DRAWINGS

The above-mentioned and other features and advantages of this disclosure, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Exemplary drug delivery devices 11, 12, and 13 are illustrated in FIGS. 1-4 and 6. Each of the shown devices 11, 12, and 13, is a reusable pen-shaped medication injection device which may be manually handled by a user (e.g., a patient, a caregiver, or a healthcare professional) to deliver a medication to a patient. Cassettes 100, 200 may also be referred to as drug delivery devices or as drug delivery cassettes. The combination of cassettes 100, 200 with a motor housing system (that may be reusable) may also be considered a drug delivery device. In certain embodiments, the user may selectively set a dose and then to inject that set dose into the patient. Devices 11, 12, 13, 100, and 200 are intended to be illustrative and not limiting as the needle assemblies described further below may be used in other differently configured devices.

The medication may be any type that may be delivered by such a device 11, 12, 13, 100, and 200. The medication may be in fluid form of various viscosities or any other suitable form. The medication includes one or more therapeutic agents including but not limited to insulins, insulin analogs such as insulin lispro or insulin glargine, insulin derivatives, GLP-1 receptor agonists such as dulaglutide or liraglutide, glucagon, glucagon analogs, glucagon derivatives, gastric inhibitory polypeptide (GIP), GIP analogs, GIP derivatives, dual agents of any combination above, such as, for example, GIP/GLP-1 receptor agonist, tirzepatide, retatrutide, oxyntomodulin analogs, oxyntomodulin derivatives, therapeutic antibodies including but not limited to IL-23 antibody analogs or derivatives, such as mirikizumab, IL-17 antibody analogs or derivatives, such as ixekizumab, therapeutic agents for pain-related treatments, such as galcanzeumab or lasmiditan, antibody analogs or derivatives related to treatment of atopic dermatitis, such a lebrikizumab, antibody analogs or derivatives related to treatment of neurodegeneration, such as donanemab, solanezumab, remternetug, and any therapeutic agent that is capable of delivery by the device 11, 12, 13, 100, and 200. The medication as used in the device 11, 12, 13, 100, and 200 may be formulated with one or more excipients.

Figure 1:
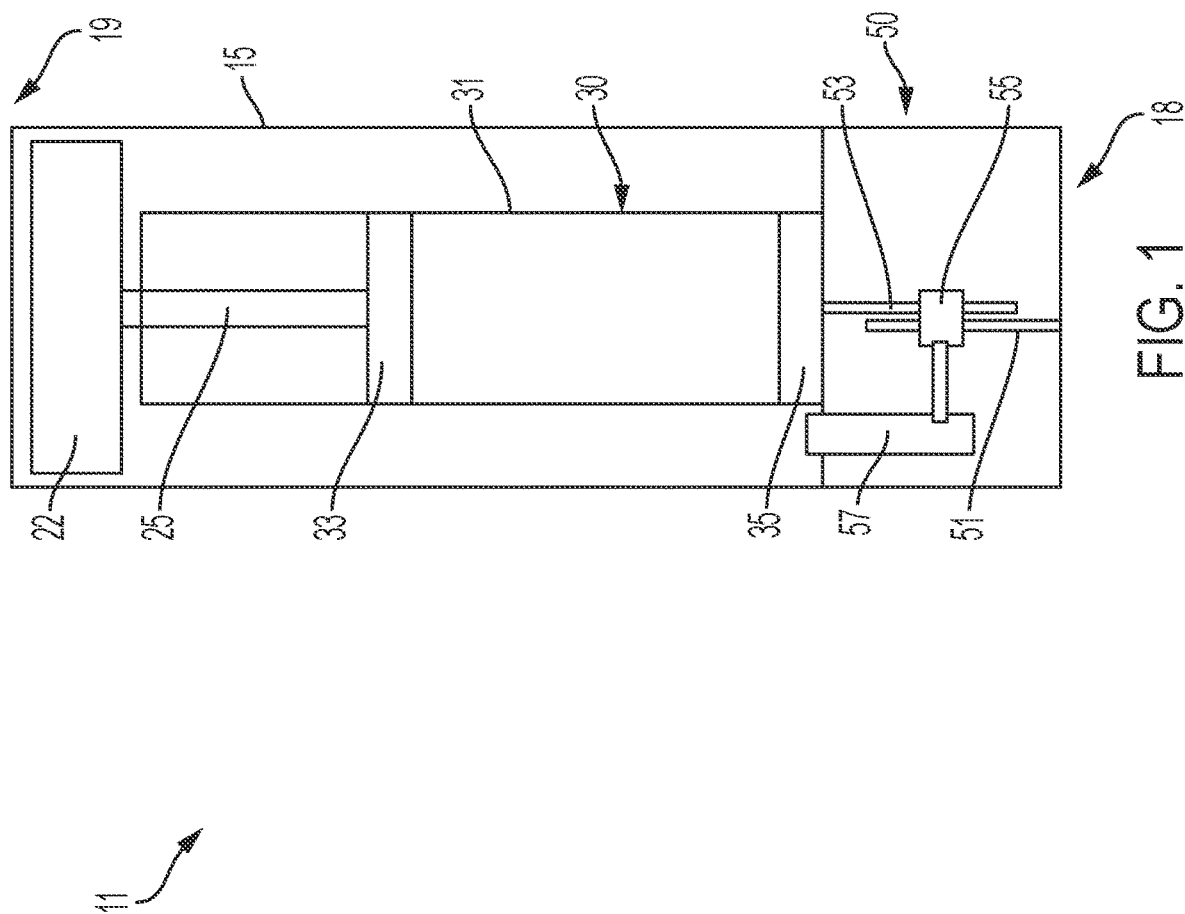
FIG. 1 is a simplified, cross-sectional view of an exemplary drug delivery device.

Referring first to FIG. 1, an exemplary embodiment of a drug delivery device 11 is shown. Drug delivery device 11 extends from a proximal end 19 to a distal end 18, and comprises a housing 15, a first motor 22, a driving system 25, a cartridge 30 configured to retain the medication, and a needle assembly 50. In the illustrated embodiment, drug delivery device 11 is configured to be positioned with distal end 18 near a patient's skin, such that needle assembly 50 may deliver the medication from within cartridge 30 to the patient. Cartridge 30 may also be described as a cassette, or a syringe, and is generally configured to contain and at least partially deliver the medication.

Cartridge 30 additionally comprises a fluid housing or barrel 31, a plunger or stopper 33, and a septum 35. The medication is retained within fluid housing 31 by stopper 33. The activation of first motor 22 actuates driving system 25 to drive stopper 33 downward to push the medication towards septum 35 and ultimately through needle assembly 50. First motor 22 may be controlled by a motor controller (not shown) to adjust the force applied to driving system 25 and/or the rate that driving system 25 is actuated.

Needle assembly 50 additionally comprises a first needle 51, a second needle 53, a needle driving mechanism 55 coupled to the first and second needles 51, 53, and an optional second motor 57 configured to actuate needle driving mechanism 55. Activation of second motor 57 actuates needle driving mechanism 55 and drives first needle 51 towards distal end 18 and drives second needle 53 towards proximal end 19 into an extended configuration whereby first needle 51 pierces at least the patient's skin, and second needle 53 pierces septum 35. In some embodiments, drug delivery device 11 only comprises first motor 22 and does not comprise the second motor 57. In such embodiments, first motor 22 may be coupled or linked to needle driving mechanism 55 such that activation of first motor 22 may additionally actuate needle driving mechanism 55. In such embodiments, the first motor 22 may actuate different aspects of the drug delivery device 11 through a clutch mechanism. As will be described in more detail later, first needle 51 and second needle 53 are fluidly coupled together to allow flow of the medication from cartridge 30, through second needle 53, through first needle 51, and ultimately to the patient.

Drug delivery device 11 is configured as a singular device and may also be configured to be disposable after use. In the illustrated embodiment, cartridge 30 and needle assembly 50 are fixedly coupled to and/or an integral part of drug delivery device 11. Cartridge 30 may contain a single dose of the medication to be delivered or may contain the medication to be delivered in multiple doses/injections. In embodiments where cartridge 30 comprises multiple doses of the medication, first motor 22 may be configured to only push out a portion of the medication within cartridge 30 for each dose, and needle assembly 50 may comprise multiple sets of needles to inject one or more medications into a patient.

Figure 2:
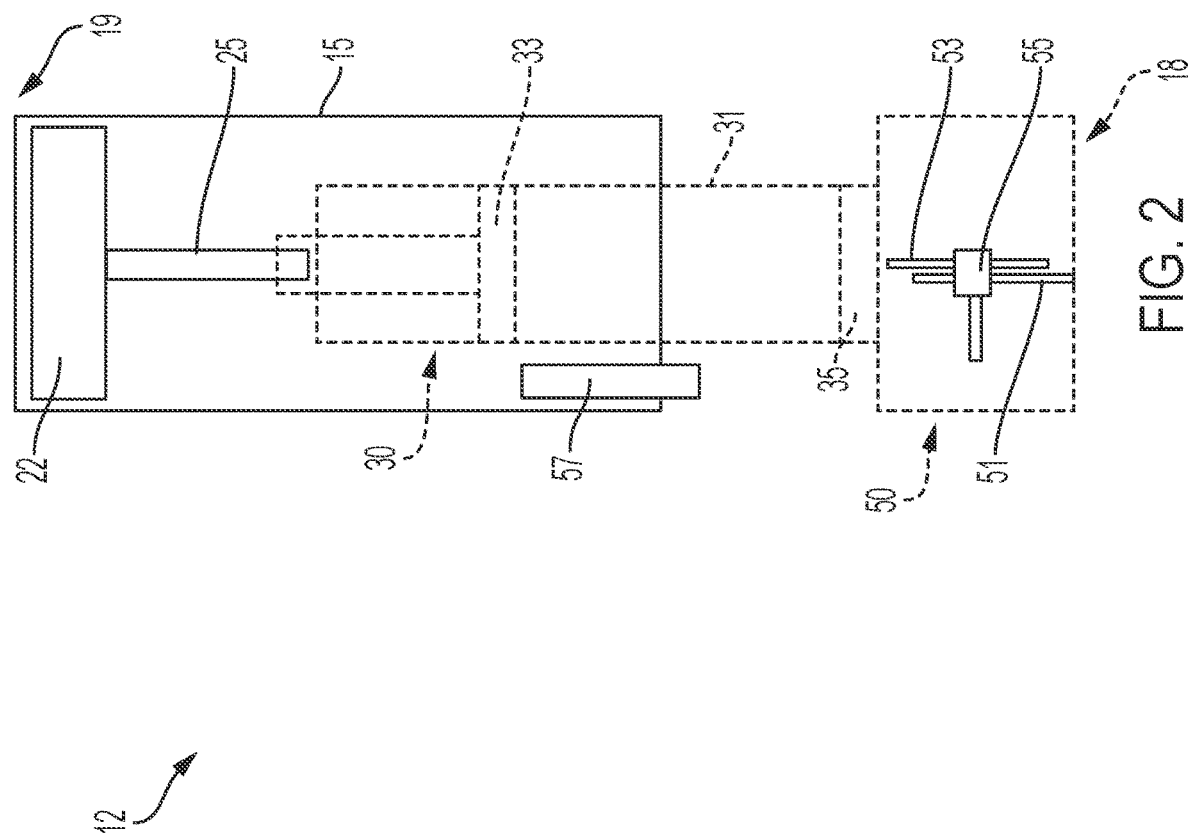
FIG. 2 is a simplified, cross-sectional view of another exemplary drug device with a detachable cassette and needle assembly.

Referring now to FIG. 2, another embodiment of a drug delivery device 12 is shown. Drug delivery device 12 functions similar to drug delivery device 11 of FIG. 1 and comprises similar components. However, drug delivery device 12 differs from drug delivery device 11 in that cartridge 30 and needle assembly 50 are removable from housing 15 of a reusable or durable housing component. Needle assembly 50 and cartridge 30 may be separate components from one another or may be one single component. In the illustrated embodiment, housing 15, first motor 22, driving system 25, and second motor 57 may all be part of the reusable housing, and cartridge 30 and needle assembly 50 may be disposable. In such an embodiment, a user may insert, use, and remove multiple instances of cartridge 30 and needle assembly 50, either together or separately. As was the case with drug delivery device 11, cartridge 30 of drug delivery device 12 may still comprise the medication for a single dose or multiple doses. Cartridge 30 and needle assembly 50 may couple to housing 15 of drug delivery device 12 through any suitable coupling mechanism, including but not limited to threading, bayonet couplers, screws, rivets, snaps, ball-detent mechanisms, spring systems, pins, magnets, friction fitting, adhesives, or any other suitable coupling device, and combinations thereof. In embodiments where cartridge 30 and needle assembly 50 are separate components, any suitable coupling device such as those mentioned above may additionally be used to couple cartridge 30 and needle assembly 50. In the illustrated embodiment, second motor 57 is coupled to housing 15, and is not shown as part of needle assembly 50 or cartridge 30, but instead couples to needle assembly 50 when needle assembly 50 is coupled to housing 15. In other embodiments, second motor 57 may be part of needle assembly 50 and may be couplable and decouplable from housing 15 with needle assembly 50.

Figure 3:
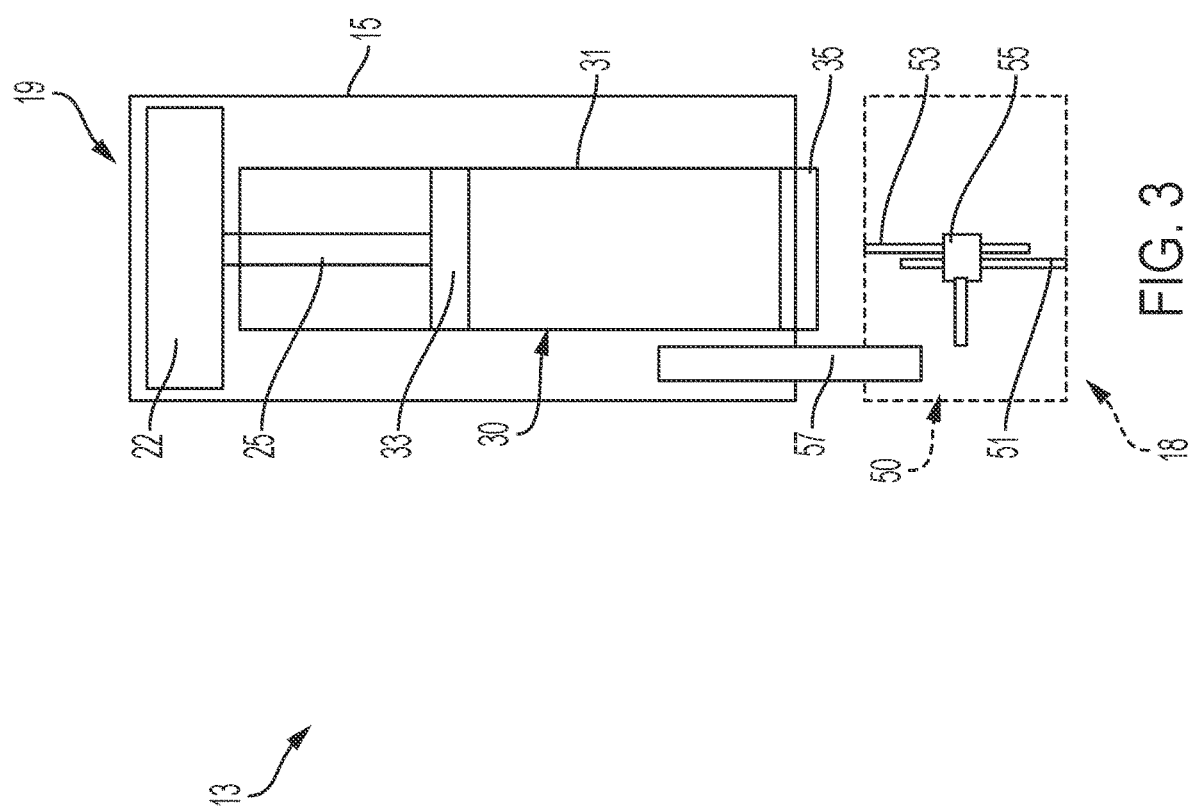
FIG. 3 is a simplified, cross-sectional view of yet another exemplary drug delivery device with a detachable needle assembly.

Referring now to FIG. 3, another embodiment of a drug delivery device 13 is shown. Drug delivery device 13 is similar to drug delivery device 11 of FIG. 1 and drug delivery device 12 of FIG. 2, except that cartridge 30 is fixedly coupled to housing 15, and needle assembly 50 is removably coupled to housing 15. Needle assembly 50 may be disposable while cartridge 30 and/or housing 15 may be reusable. In the illustrated embodiment, housing 15 and cartridge 30 may be used multiple times with different instances of needle assembly 50. In some embodiments, cartridge 30 may be refillable with the medication. As mentioned before with respect to drug delivery device 12, needle assembly 50 may be coupled to housing 15 through any suitable coupling device or system. Additionally, second motor 57 may be part of housing 15 or needle assembly 50. Additional embodiments, configurations, and details of drug delivery devices and their components will be discussed below.

Figure 4:
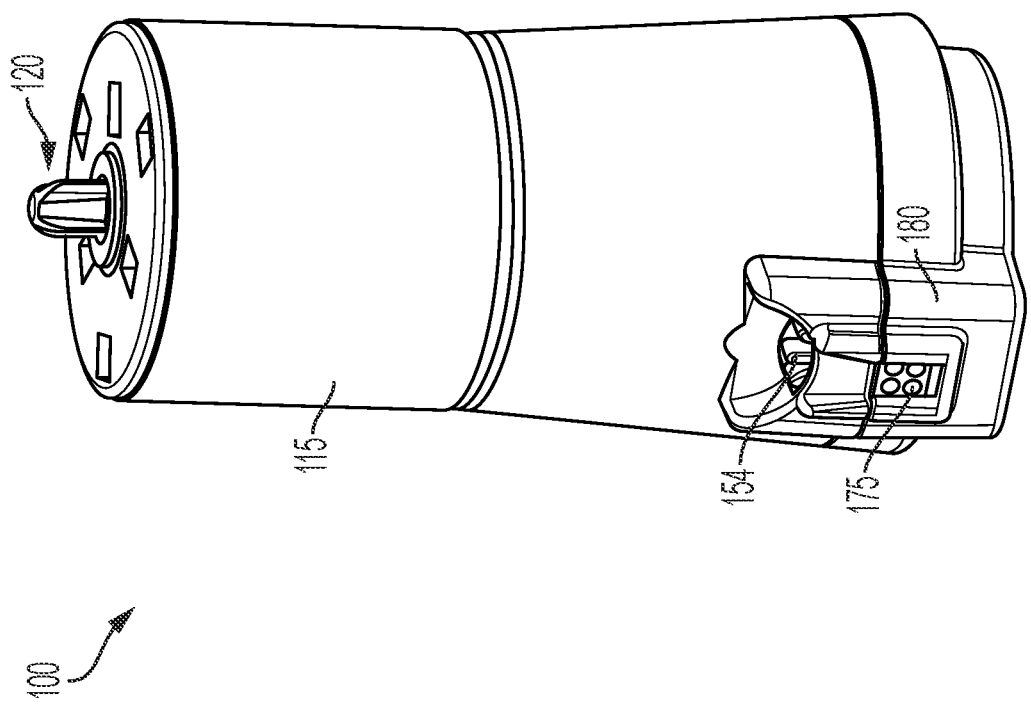
FIG. 4 is a perspective view of yet another exemplary drug delivery device.
Figure 5:
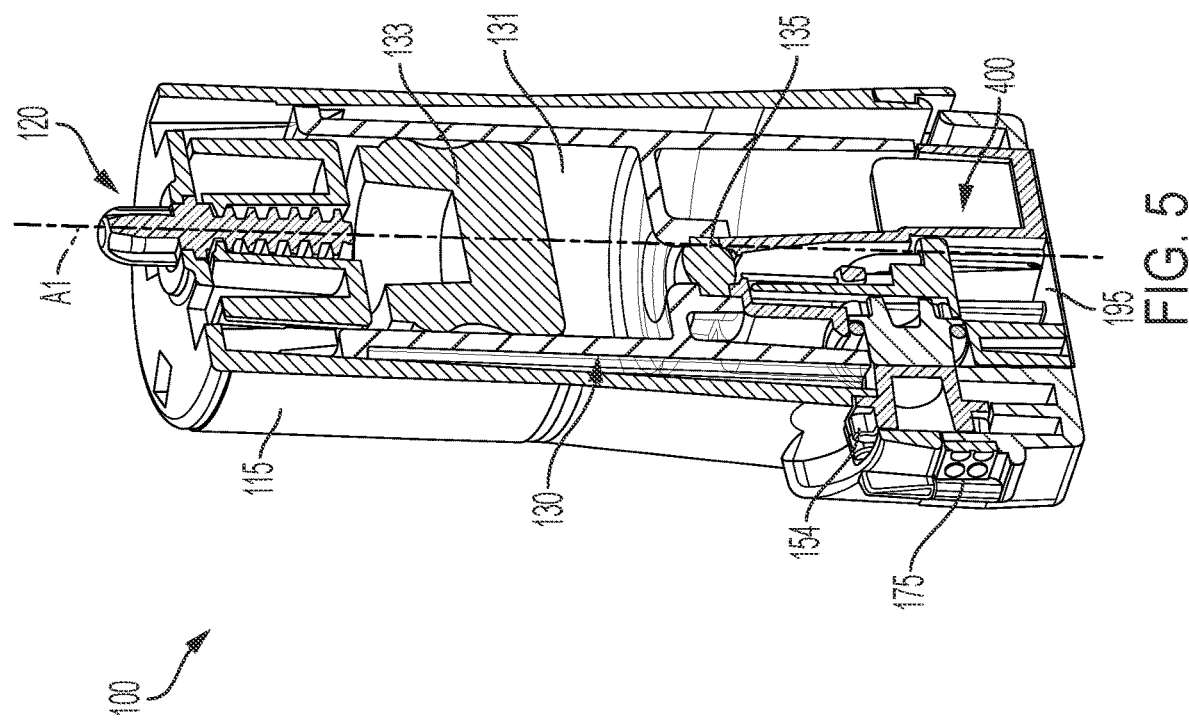
FIG. 5 is a cross-sectional view of the device of FIG. 4.

Referring now to FIGS. 4-5, a cassette 100 for another embodiment of a drug delivery device like the one in FIG. 2 is shown. Cassette 100 comprises one or more of the following: a housing 115, a stopper driving system 120, a cartridge 130 which may be coupled to or integrally formed with housing 115, a stopper 133, a fluid housing 131, a septum 135, a cassette ID 175, an orientation mechanism 180, a needle assembly 400, and a needle assembly actuating gear 154. The cassette 100 may also comprise a reusable or durable housing (not shown) to which the housing 115 may be coupled. The reusable housing may also comprise a number of motors, such as the first motor 22 and second motor 57 described above, as well as a controller, processor, memory, user interface, and/or other features configured to interact with cassette 100.

Cassette 100 is configured to retain a volume of a medication within fluid housing 131, and to deliver the medication to a patient in a similar fashion to devices 11, 12, and 13 described above. Actuation of the needle assembly actuating gear 154 causes the needle assembly 400 (See FIG. 29) to extend, piercing the septum 135 with a first needle, and a surface such as a patient's skin with a second needle. The cassette 100 may also comprise a seal 195 configured to seal at least a portion of needle assembly 400 within cassette 100 before the extension of the second needle. The seal 195 may also maintain a sterile environment within cassette 100. When extended, needle assembly 400 provides fluid communication between the fluid housing 131 and the second needle. A motor and/or a user-activated actuator (e.g. a button, a knob, a plunger, etc.) may then cause stopper 133 to drive the medication out of fluid housing 131 through needle assembly 400 and to a patient. Needle assembly 400 may then be retracted through actuation, such as reverse actuation, of needle assembly actuating gear 154.

The orientation mechanism 180 is configured to orient at least a portion of cassette 100 rotationally around a central axis A1. For example, orientation mechanism 180 may orient housing 115 at a particular angular orientation with respect to a reusable housing or with respect to a motor or actuation device. In the illustrated embodiments, orientation mechanism 180 is shown as a radial protrusion. The reusable housing or other device that contains a motor or actuation device comprises a complimentary recess or slot to receive the orientation mechanism 180. Accordingly, when a user couples cassette 100 to the reusable housing, cassette 100 may be restricted to a certain orientation with respect to the reusable housing Achieving a desired orientation may allow a motor or other actuation device to operably couple with needle assembly actuating gear 154 and/or stopper driving system 120. The desired orientation may also allow for cassette ID 175 to be positioned such that it may be read or scanned by a cassette ID reading system. Additionally, the orientation mechanism 180 may orient the cassette 100 with respect to a patient's skin, and/or orient the needle assembly 400 with respect to any other component of cassette 100. While orientation mechanism 180 is illustrated as a protrusion, orientation mechanism 180 may also be a slot to interface with a protrusion on a reusable housing. Furthermore, orientation mechanism 180 may be a gear, a ramped or curved surface, a knob, a plurality of protrusions or slots, a screw, or any other mechanism configured to orient cassette 100. In another embodiment, the loading of the cassette into the reusable housing is axial, whereas there are other embodiments where the loading of the cassette is radially into the reusable housing.

Any components of cassette 100, such as housing 115, cartridge 130 and/or fluid housing 131 may be composed of a polymer. Utilizing a polymeric cartridge instead of a standard glass cartridge provides more flexibility when manufacturing cassette 100. For example, a polymeric cartridge may be shaped differently than standardized glass cartridges, allowing for a more compact design while maintaining the same volume as a standard glass cartridge.

Furthermore, polymeric cartridges may be more easily manufactured, disposed of, and/or recycled compared to glass cartridges. Additionally, polymeric cartridges may be manufactured to directly interact with or couple with other components of cassette 100. For example, cartridge 130 may couple with needle assembly 400 without the need for additional coupling components (e.g., fasteners), since cartridge 130 may be manufactured with integral coupling features, or may be integrally formed with needle assembly 400. As another example, and as discussed above, cartridge 130 may be coupled to or integrally formed with housing 115.

Use of polymeric material may reduce the form factor or aspect ratio of cassette 100 in comparison to a cassette that utilizes a standard glass cartridge, which may allow for more compact or efficient packaging. The cassette 100 may have a height of less than 75 mm, less than 70 mm, less than 65 mm, less than 60 mm, less than 55 mm, less than 50 mm, less than 45 mm, less than 40 mm, or any range including any two of these values as endpoints. The cassette 100 may have a diameter of less than 50 mm, less than 45 mm, less than 40 mm, less than 35 mm, less than 30 mm, less than 25 mm, less than 20 mm, less than 15 mm, or any range including any two of these values as endpoints. More specifically, the cassette may have a height from 45 mm to 60 mm, and a diameter of 25 mm to 35 mm. Stated differently, the cassette 100 may have an aspect ratio of height:diameter of X:Y where X and Y are each independently 5, 4.75, 4.5, 4.25, 4, 3.75, 2.5, 3.25, 3, 2.75, 2.5, 2.25, 2, 1.75, 1.5, 1, or any range including any two of these values as endpoints. For example, cassette 100 may have an aspect ratio from 2:1 to 1:1.

Reducing the aspect ratio of the cassette 100 and/or cartridge 130 may also reduce the distance that the stopper or a plunger may have to travel in delivery of medication. A standard 1.6 mL glass cartridge may have an inner diameter of around 9.25 mm, and require a stopper to travel at least 14 mm to fully deliver 1 mL of a medication from the cartridge. A standard 3.0 mL glass cartridge may have an inner diameter of around 9.7 mm, and may require a stopper to travel at least 13 mm to fully deliver 1 mL of medication from the cartridge. Alternatively, the cartridge 130 of cassette 100 may require a stopper travel distance of less than 10 mm, less than 9 mm, less than 8 mm, less than 7 mm, less than 6 mm, less than 5 mm, or any range including any two of these values as endpoints in order to fully deliver a medication from cartridge 130. Stated differently, the ratio of the distance of stopper 133 travel to fully deliver a medication to the inner diameter of the cartridge 130 may be A:B where A and B are independently 1, 1.25, 1.5, 1.75, 2, 2.25, 2.5, 2.75, 3, or any range including any two of these values as endpoints. For example, the ratio of A:B may be from 1:1 to 1:3, or more particularly from 1:1.5 to 1:2.5. "Fully delivered" indicates that a full cartridge is essentially completely emptied of medication. Reduction in stopper travel length may reduce the complexity of moving parts within cassette 100 or within the overall drug delivery device. The volume of the cassette may provide any volume of medication, such as 0.5 mL, 1.0 mL, 2.0 mL, 3.0 mL, 10 mL, or the like.

In the illustrated embodiments, cassette ID 175 is positioned on the orientation mechanism 180. Cassette ID 175 may be any sort of mechanism or device that provides data about a component of cassette 100. For example, Cassette ID 175 may comprise a chip, an RFID indicator, a unique coded pattern, and/or an antenna that provides data regarding the type of medication within cassette 130 (e.g. specific medication, viscosity, volume, dosage, injection scheduling, etc.). The cassette ID 175 may also provide data related to the orientation or assembly of the cassette 100 (e.g. indicating whether or not the device is fully or properly assembled, whether the device is in the proper orientation, etc.). The cassette ID 175 may provide data from a sensor or a plurality of sensors within cassette 100, such as a position sensor, a fluid level sensor, a damage or failure sensor, a battery level sensor, and/or a pressure sensor.

Figure 6:
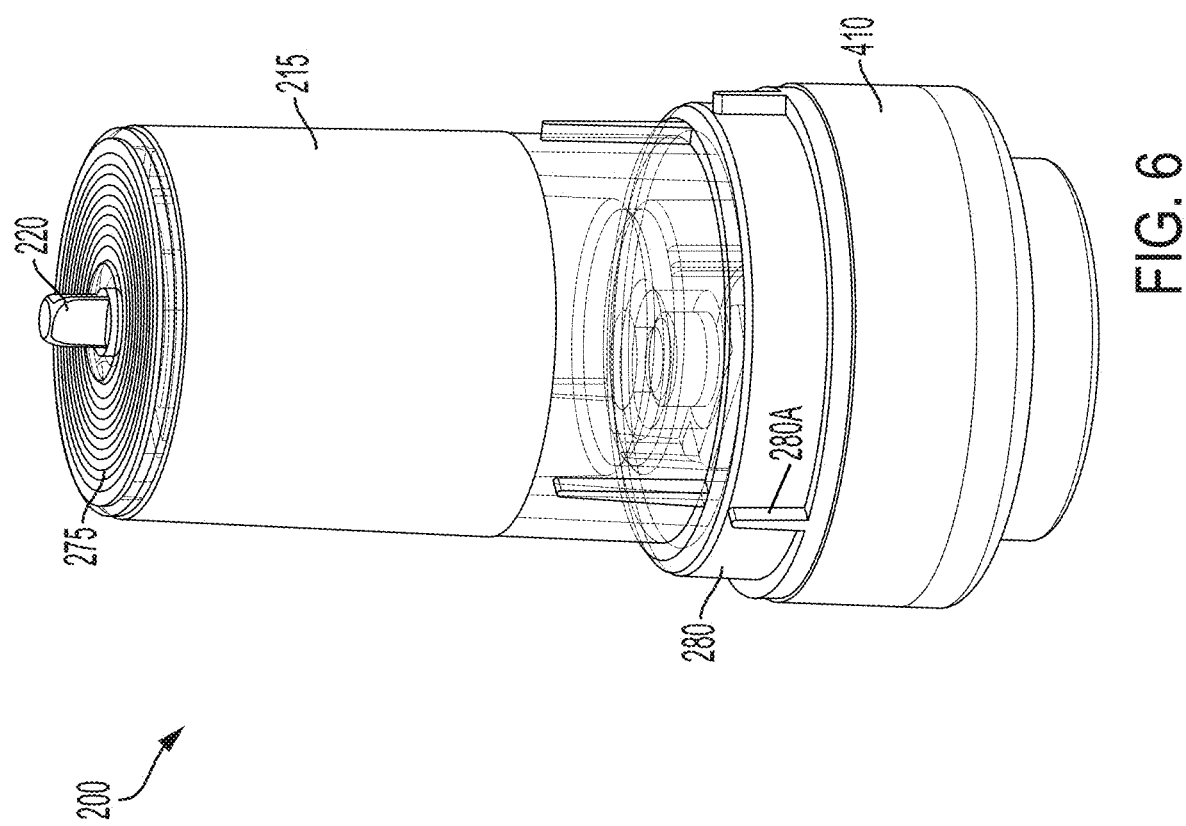
FIG. 6 is a perspective view of still another exemplary drug delivery device.
Figure 7:
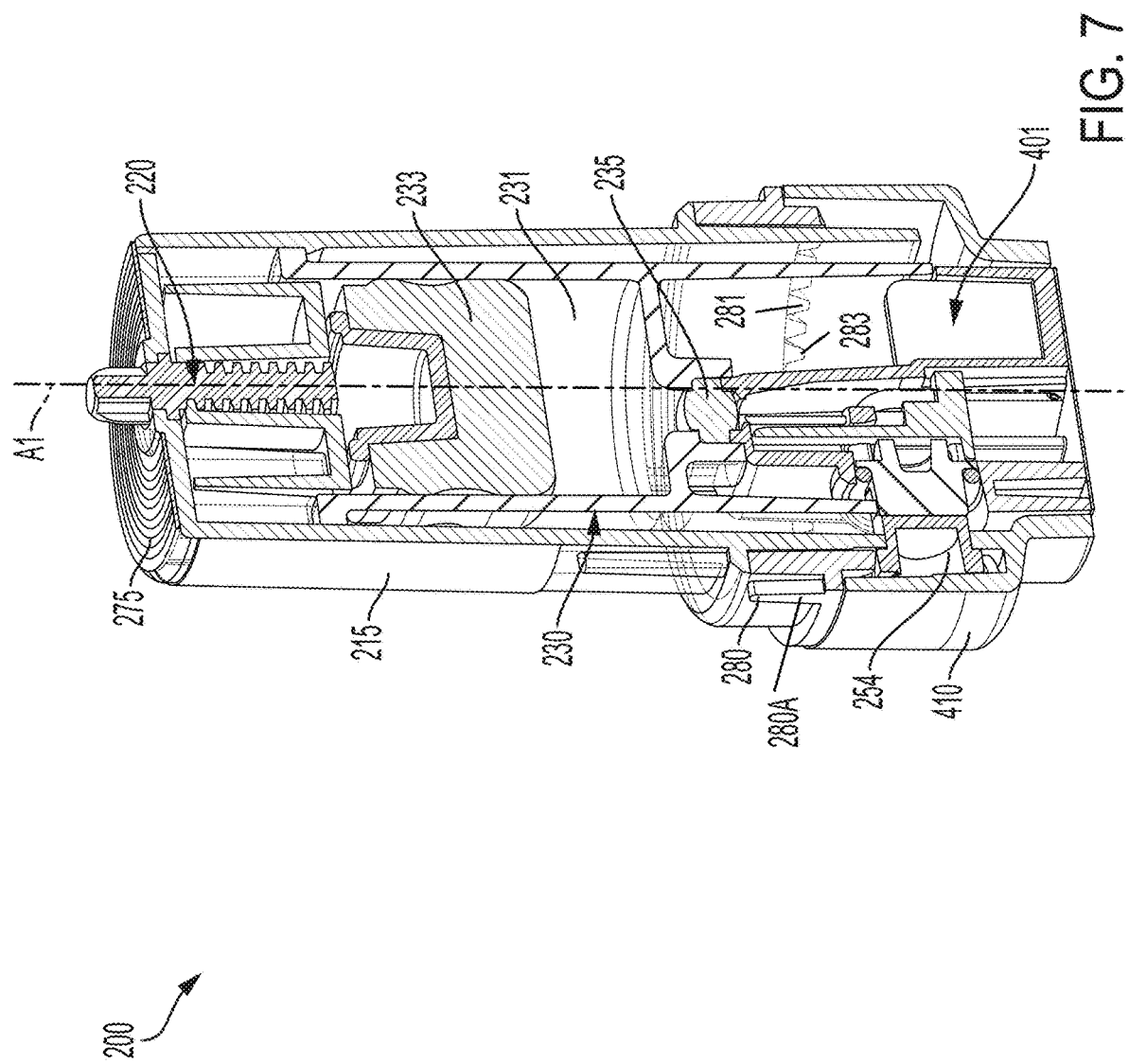
FIG. 7 is a cross-sectional view of the device of FIG. 6.

Referring now to FIGS. 6-7, another embodiment of a cassette 200 is shown. Cassette 200 is similar to cassette 100 in overall operation and comprises similar components. Cassette 200 comprises a housing 215, a stopper driving system 220, a cartridge 230, a stopper 233, a fluid housing 231, a septum 235, a cassette ID 275, a needle assembly 401, and a needle assembly actuating gear 254. Cassette 200 and its components function in a similar fashion and have similar features as the corresponding components in cassette 100. Furthermore, any reference to cassette 100 herein may be applied to cassette 200.

Cassette 200 also comprises an external gear 280 which is configured to interface with needle assembly actuating gear 254 to actuate needle assembly 401. A motor or a user-activated actuator from the reusable module may rotate external gear 280 which in turn may rotate relative to a lower housing 410 and cartridge 230 to rotate needle assembly actuating gear 254 to actuate needle assembly 401, as will be described in additional detail herein. External gear 280 may comprise external gear teeth or other interface features 280A (see FIG. 33) to be driven by a motor or other actuating device, such as the second motor 57. Cassette 200 may be configured such that it may be oriented in any axial/rotational position around central axis A1 when coupled to a reusable or reusable housing. While cassette 100 comprises orientation mechanism 180 to orient cassette 100 relative to a housing, cassette 200 may not require any similar orientation. In some embodiments, external gear 280 may function as an orientation mechanism, similar to orientation mechanism 180, to rotate cassette 200 or components thereof around central axis A1. A clutch or similar mechanism may be employed to cause the rotation of external gear 280 to rotate all of or a portion of cassette 200, and the clutch may be activated to cause rotation of external gear 280 to then rotate needle assembly actuating gear 254. Accordingly, external gear 280 may be utilized to orient components of cassette 200 with respect to a reusable housing, a motor, or another device external to cassette 200. In some embodiments, cassette 200 may not need to be oriented relative to any other component, and may be assembled or coupled with a reusable housing in any axial position.

The cassette ID 275 of cassette 200 may be implemented such that a particular angular orientation can be avoided. For example, the cassette ID 275 is illustrated as a series of concentric rings on a proximal end of cassette 200. Cassette ID 275 may be referred to as a circular cassette ID. Cassette ID 275 functions similarly to cassette ID 175, with a different position and layout. Because cassette ID 275 extends entirely around the proximal end of cassette 200, the cassette ID 275 may be read when cassette 200 is in any rotational position along its central axis A1. Accordingly, cassette 200 may not require rotational orientation to allow for reading of cassette ID 275. Additionally, in embodiments where cassette 200 may be rotated by external gear 280, cassette ID 275 may still be read from any rotational position.

Figure 8:
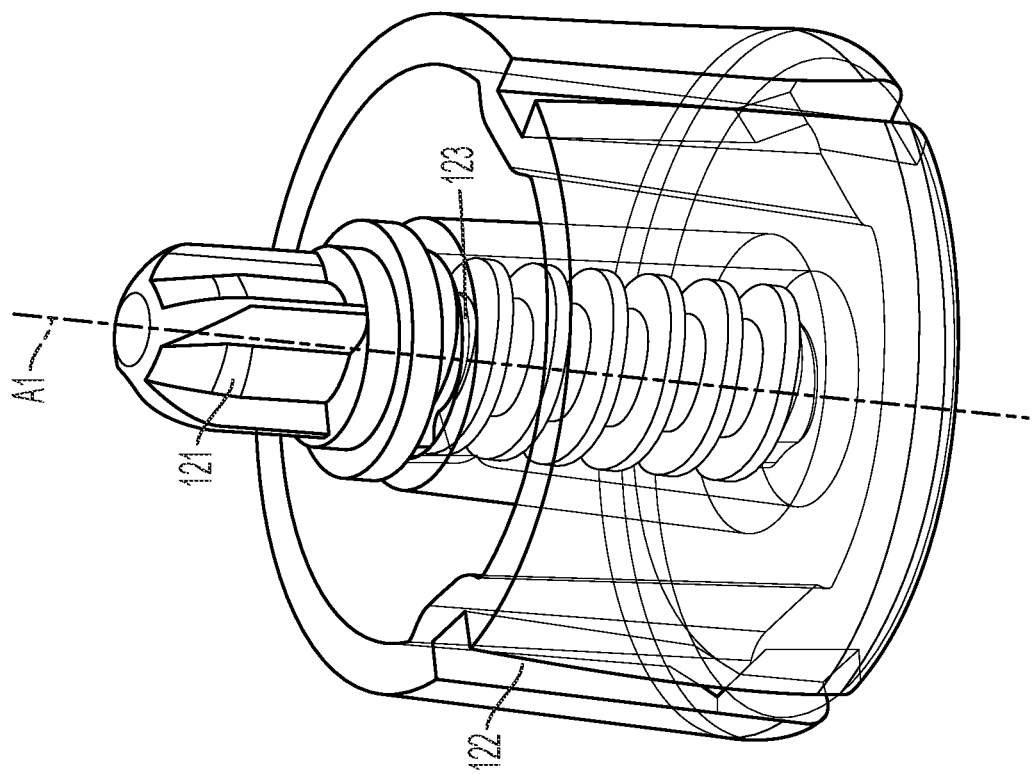
FIG. 8 is a perspective view of a driving system of the device of FIG. 4.

Referring to FIG. 8, the stopper driving system 120 is shown. Stopper driving system 120 comprises a driven body 122, a driving screw 123, and an interfacing end 121. The interfacing end 121 is configured to interact with a motor or another actuating device (e.g. a knob). Rotation of interfacing end 121 causes rotation of driving screw 123. Driving screw 123 is threadedly engaged with driven body 122, such that rotation of driving screw 123 causes movement of driven body 122 up or down along a central axis A1. Driven body 122 may be in direct contact with a medication within fluid housing 131 (FIG. 5) or may be in contact with a stopper that contacts the medication. Actuation of stopper driving system 120 pushes the medication out of fluid housing 131. All features of stopper driving system 120 may also apply to driving system 220 of cassette 200. Other exemplary embodiments of driving systems 250 are described in PCT Publication No. WO 2019/112886, the entire disclosure of which is incorporated by reference herein.

Figure 9:
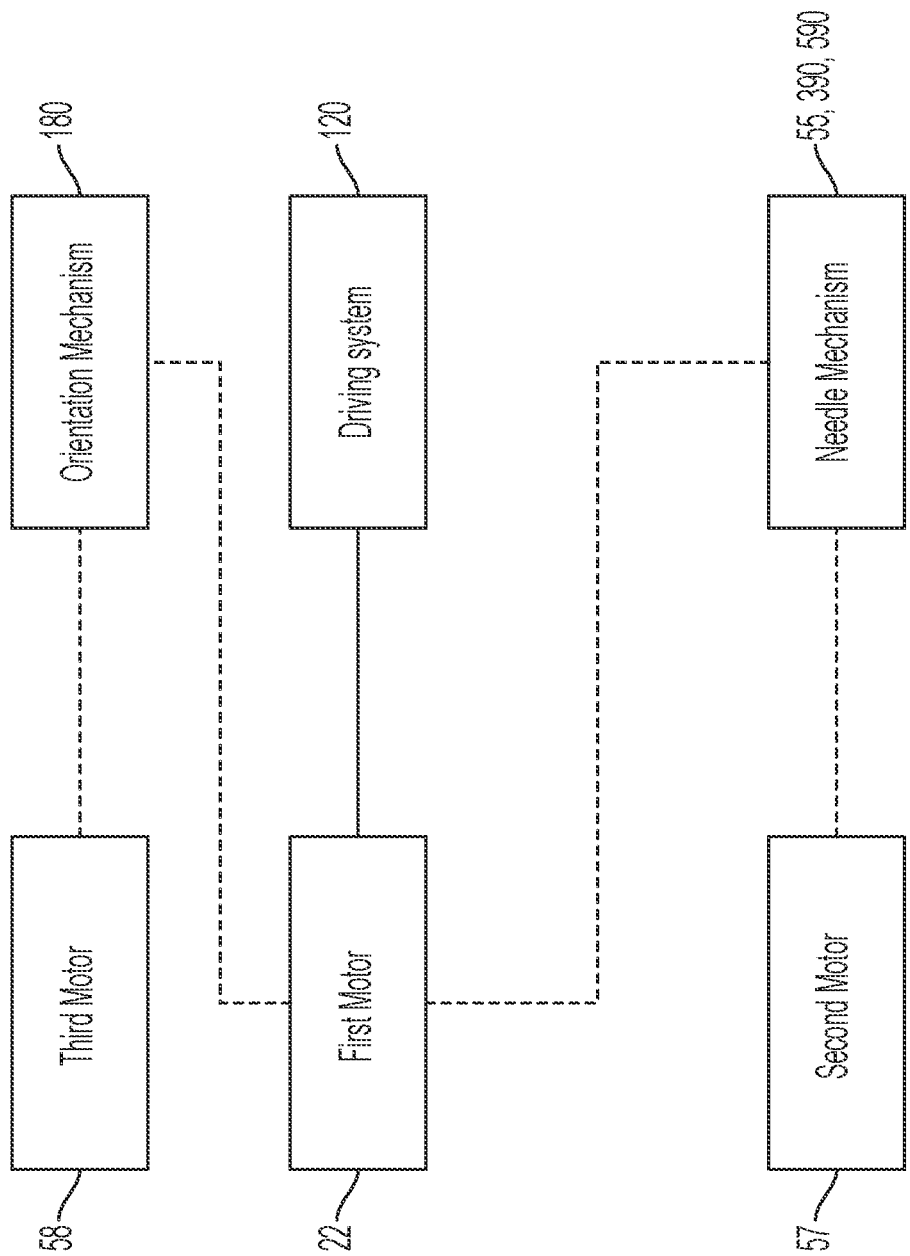
FIG. 9 is a diagrammatic view of the driving system of FIG. 8.
Figure 10:
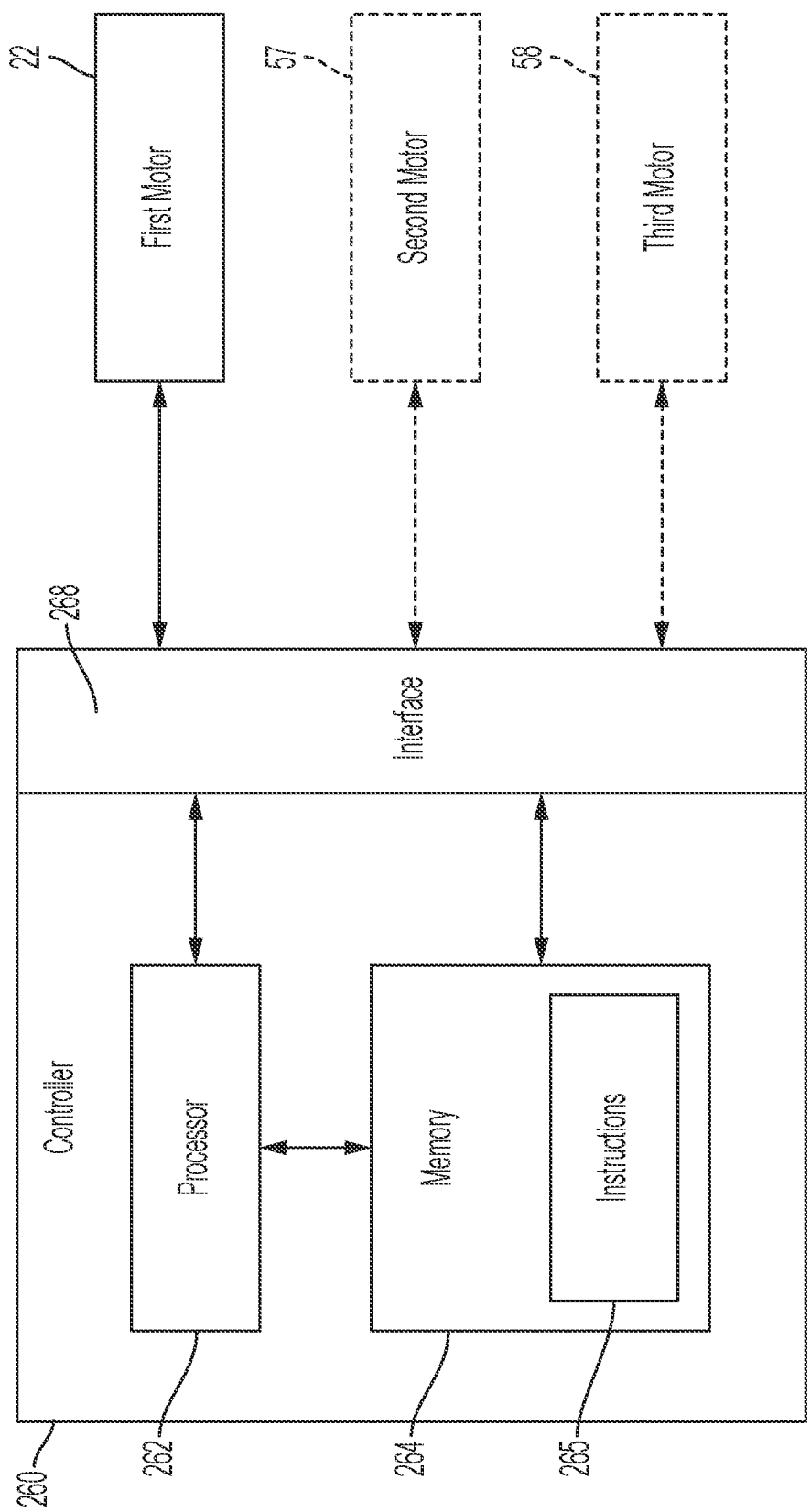
FIG. 10 is a diagrammatic view of a control system for the driving system of FIG. 8.
Figure 11:
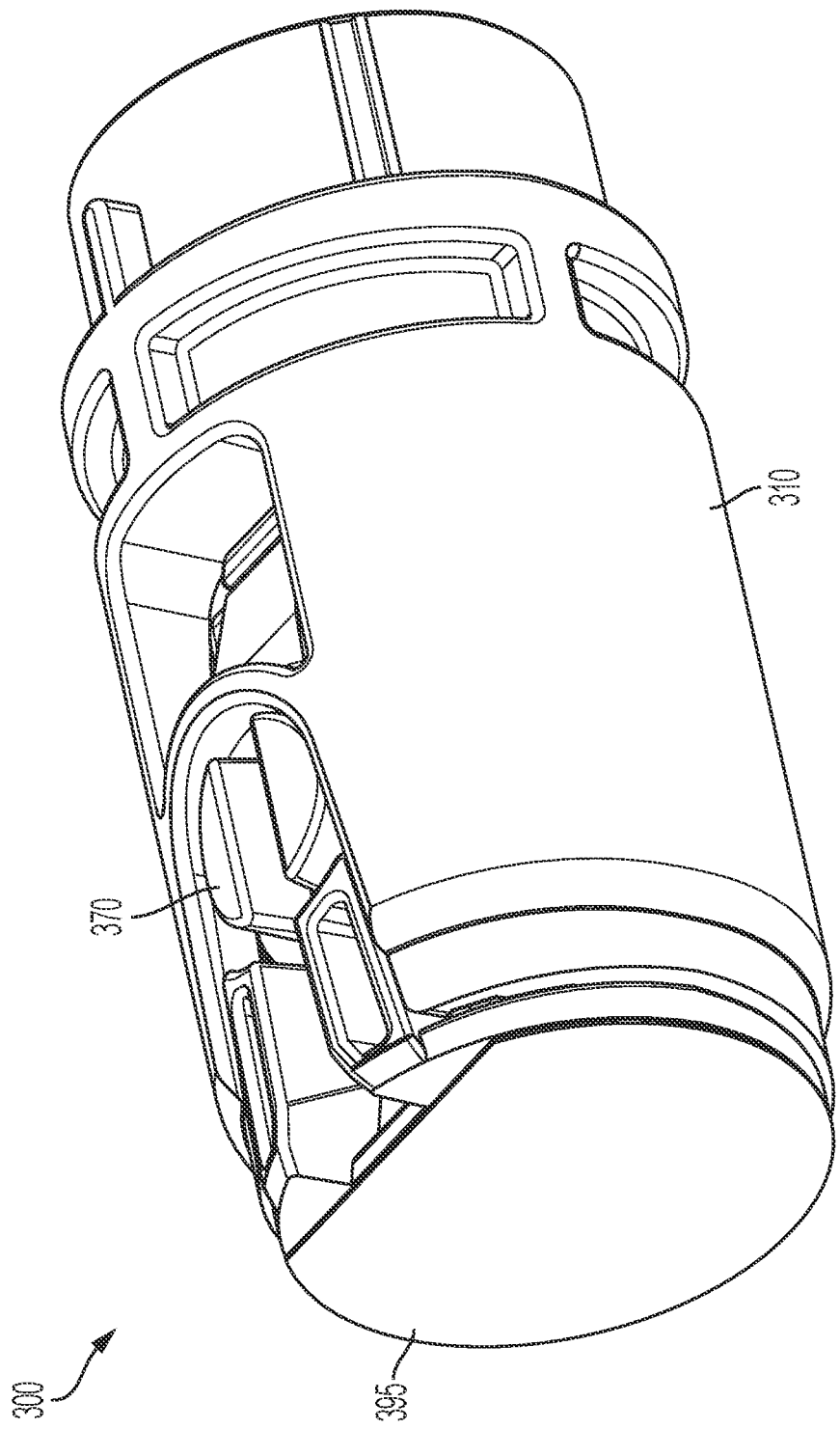
FIG. 11 is a perspective view of an exemplary needle assembly.
Figure 12:
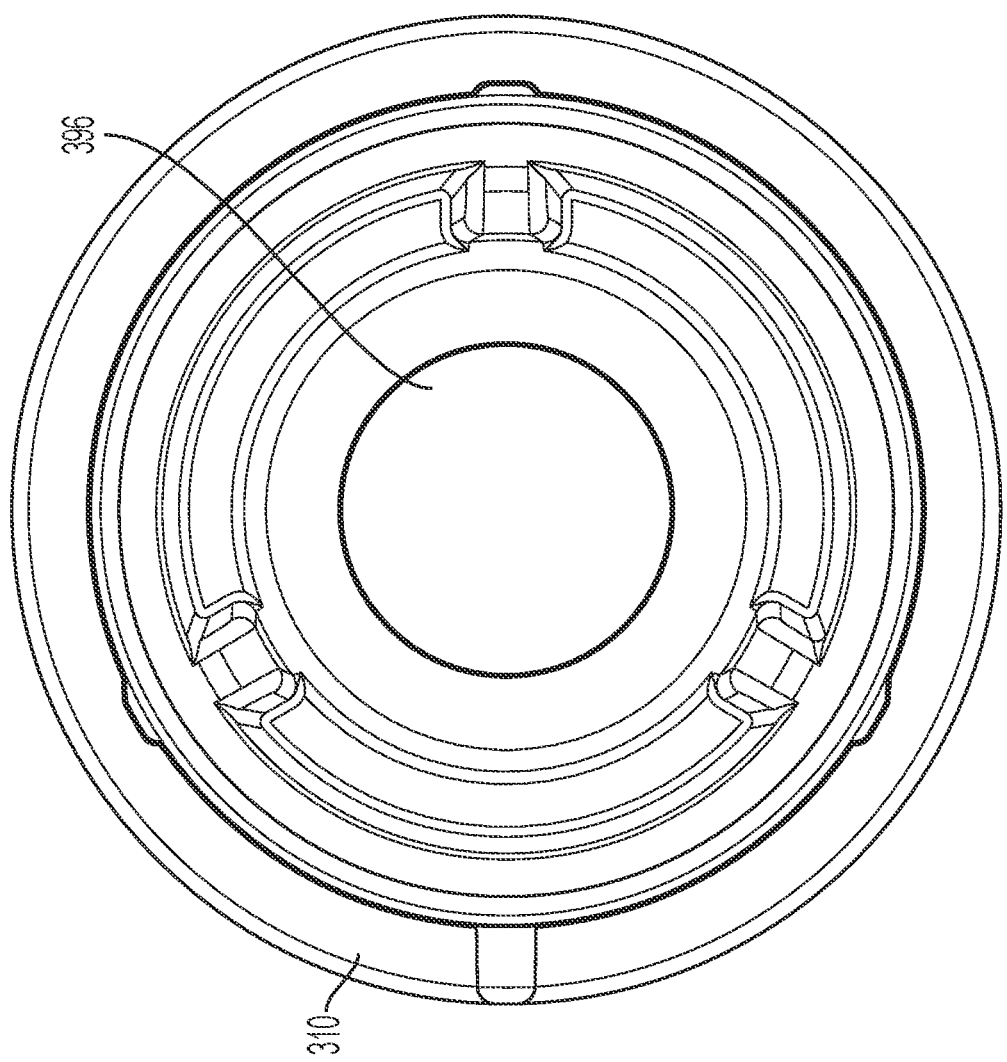
FIG. 12 is a rear view of the needle assembly of FIG. 11.
Figure 13:
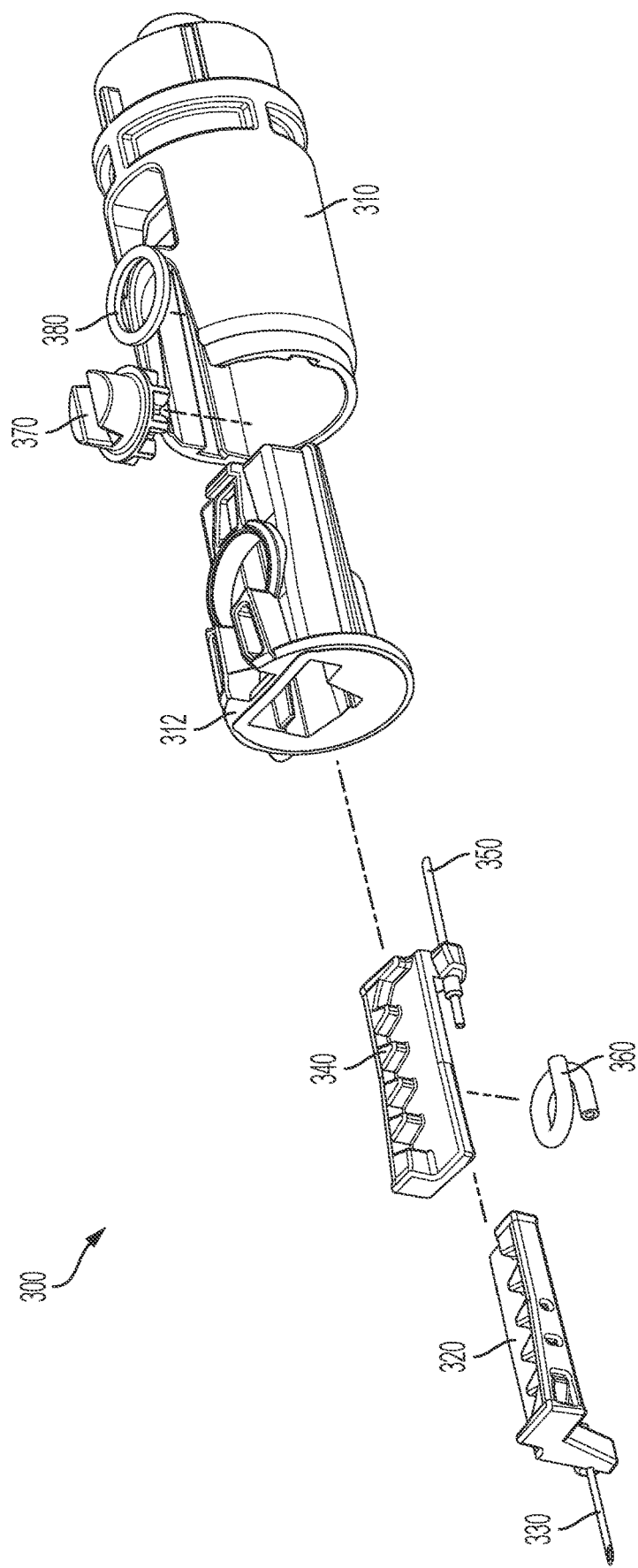
FIG. 13 is an exploded view of the needle assembly of FIG. 11.

Referring to FIGS. 9-10, first motor 22 is operably coupled to stopper driving system 120 such that activation of first motor 22 actuates stopper driving system 120. Additionally, cassette 100 optionally comprises a second motor 57 (as shown in FIGS. 1-3), configured to actuate a needle mechanism, such as any of the needle mechanisms 55, 390, 590 described herein. Cassette 100 may also optionally comprise a third motor 58 configured to drive orientation mechanism 180 in embodiments where the orientation mechanism 180, 280 is a gear or another actuatable device. In embodiments where the drug delivery device does not comprise second motor 57, first motor 22 may be configured to actuate the needle mechanism(s) 55, 390, 590. In embodiments were the drug delivery device does not comprise a third motor 58, first motor 22 may be configured to actuate the orientation mechanism 180. In embodiments where the orientation mechanism 180, 280 may also actuate the needle mechanism 55, 390, 590, the second motor 57 or the third motor 58 may actuate both the orientation mechanism 180, 280 and the needle mechanism 55, 390, 590.

Each of the motors 22, 57, and 58 may be coupled to a reusable housing of cassette 100, and/or coupled to cartridge 130. In some embodiments, at least one motor 22, 57, and 58 is coupled to the reusable housing, and orientation mechanism 180 is configured to orient cartridge 130 with respect to the reusable housing and the at least one motor 22, 57, 58, such that cartridge 130 and/or a component of cartridge 130 is operably coupled to the at least one motor 22, 57, 58. For example, orientation mechanism 180 may be configured to orient cartridge 130 such that stopper driving system 120 is operably coupled to a motor 22, 57, 58. Orientation mechanism may orient a needle assembly 300, 400, 401, 500 relative to a reusable housing or a motor such that needle assembly 300, 400, 401, 500 and/or needle mechanism 55, 390, 590 are operably coupled to motor 22, 57, 58.

In one embodiment, a disposable medication cassette unit is provided for attachment and detachment from a reusable housing unit configured to receive the cassette unit. The cassette unit includes a cassette unit body extending along the central axis A1 between a proximal end and a distal end. The proximal and distal ends may be defined by planar surfaces extending perpendicular to the central axis A1. Extending beyond the proximal end of the cassette unit is the interfacing end of the stopper driving system. The interfacing end is exposed outside the body of the cassette unit and disposed along the central axis A1. The unit body includes a proximal sleeve portion extending along a proximal portion of the cassette and a distal portion surrounding the needle assembly. Between the portions there can be an intermediate portion that is made of a material to allow the visibility of the cassette contained within.

Each of the first motor 22 and optional second motor 57 and optional third motor may be controlled by a motor controller 260. The term "logic" or "control logic" as used herein may include software and/or firmware executing on one or more programmable processors, application-specific integrated circuits (ASICs), field-programmable gate arrays (FPGAs), digital signal processors (DSPs), hardwired logic, or combinations thereof. Therefore, in accordance with the embodiments, various logic may be implemented in any appropriate fashion and would remain in accordance with the embodiments herein disclosed. Controller 260 may be included in cassette 100 or may be external. Controller 260 may include at least one processor 262 (e.g. microprocessor) that executes software and/or firmware stored in a memory 264 of controller 260. The software/firmware code contains instructions 265 that, when executed by the processor 262, cause controller 260 to perform the functions of the control algorithm described herein. Controller 260 may receive information from a plurality of system components and feed the information (e.g. medication data, patient data, drug delivery device data, needle assembly data) into the control algorithm which determines at least one drug delivery control parameter which may in part govern operation of first motor 22, second motor 57, and/or third motor 58. Controller 260 may include or be communicatively coupled to one or more interfaces to communicatively couple via one or more communication links to the cassette 100. Examples interfaces include wired and wireless signal transmitters and receivers. Example communication links include a wired communication link (e.g. a serial communication), a wireless communication link such as, for example, a short-range radio link, such as Bluetooth, IEEE 802.11, a proprietary wireless protocol, and/or the like. The term "communication link" may refer to an ability to communicate some type of information in at least one direction between at least two devices. The communication links may be a persistent communication link, an intermittent communication link, an ad-hoc communication link, and/or the like. Information may be transmitted via the communication links.

FIG. 10 shows the controller 260 including memory 264 and processor 262 communicatively coupled to the one or more interfaces 268 and to each other. The memory 264 may include computer-readable storage media in the form of volatile and/or nonvolatile memory and may be removable, non-removable or a combination thereof. In embodiments, memory 264 stores executable instructions 265 (e.g. computer code, machine-useable instructions, and the like) for causing processor 262 to implement aspects of embodiments of system components discussed herein and/or to perform aspects of embodiments of methods and procedures discussed herein, including the control logic described in more detail below. The memory 264, processor 262, and interfaces 268 may be communicatively coupled by one or more busses. The data and/or information may be provided to controller 260 as acquired, on a predefined schedule, or queued inn memory and supplied to controller 260 when requested.

The logic of controller 260 may be configured to adjust the rate of actuation or the force of actuation provided by first motor 22, second motor 57, and/or third motor 58. For example, if the medication in cartridge 130 is viscous, the force applied by first motor 22 to drive stopper 133 may be increased. In a further example, the rate of actuation for the first or second motor 22, 57 may be adjusted to alter the rate of actuation for the needle mechanism. The needle mechanism may be actuated more slowly to improve patient comfort and reduce irritation. In some embodiments, the controller may alter the operating parameters of first and/or second motor 22, 57 based on received information/data (e.g. patient data, medication data, historical use data, dose data, drug delivery device data, needle assembly data, cartridge data). Additionally, controller 260 may be configured to alter the speed of motors 22, 57 over the course of activation such that motion of stopper driving system 120 and/or the needle mechanism is not constant or non-linear. For example, needle mechanism may be actuated such that the needles decelerate near the end of travel to prevent a hard stop. Controller 260 may also control timing of motor activation, for example activating first motor 22 before second motor 57. Controller 260 may also receive data based on needle position indicating the location of at least one needle in the needle assembly, and may alter the speed, force, or positioning of the at least one needle based on the position data.

Referring now to FIGS. 11-14, an exemplary embodiment of a needle assembly 300 is shown. Any of the illustrated needle assemblies or variations thereof may be used within cassette 100. Furthermore, the needle assemblies disclosed may be used separately from cassette 100, for example in chemical sampling instrumentation, or in other applications where a needle is used. Needle assembly 300 comprises an assembly housing 310, an internal housing 312, a first needle support 320 coupled to a first needle 330, a second needle support 340 coupled to a second needle 350, a movable connector 360, a driving member 370, and an O-ring 380. Furthermore, needle assembly 300 comprises an exterior seal 395 and an interior seal 396. Together, first needle support 320, first needle 330, second needle support 340, second needle 350, movable connector 360, and movable connector 360 comprise a needle mechanism 390. The exterior seal 395 and interior seal 396 are configured to seal the needle mechanism 390 within the needle assembly 300 before the needle assembly 300 is used and also to help maintain sterile conditions within needle assembly 300. In some embodiments, interior seal 396 may not be included, and the coupling between needle assembly 300 and the rest of the cassette 100 may maintain sterility. Description of aspects of the drug delivery device and the needle assembly 300 can be found in PCT Publication No. WO2022/132675, filed on Dec. 14, 2021, titled "FLUID DELIVERY SYSTEM WITH NEEDLE ASSEMBLY", the entire disclosure of which is incorporated by reference herein.

Figure 14:
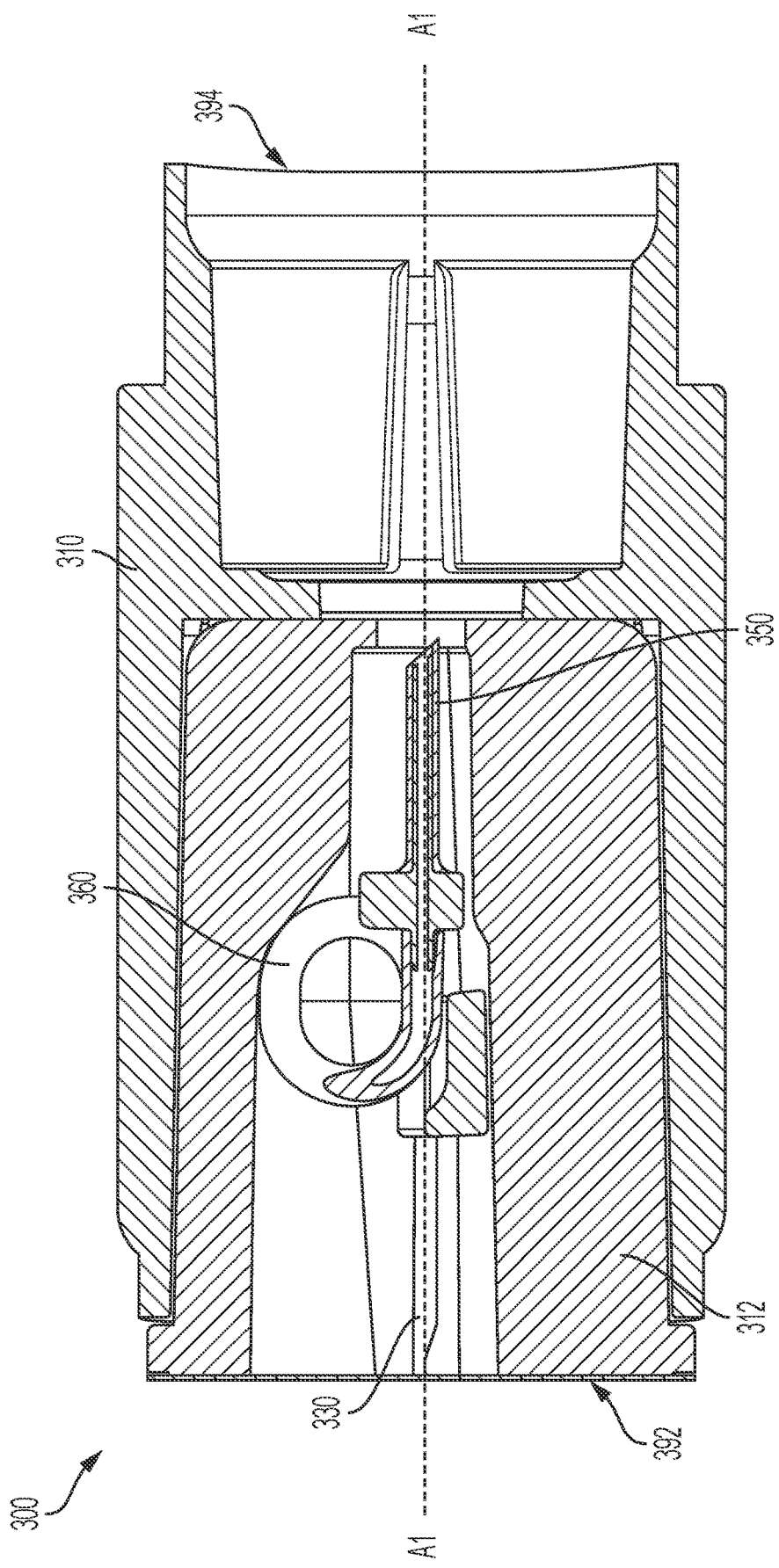
FIG. 14 is a cross-sectional view of the needle assembly of FIG. 11.
Figure 16:
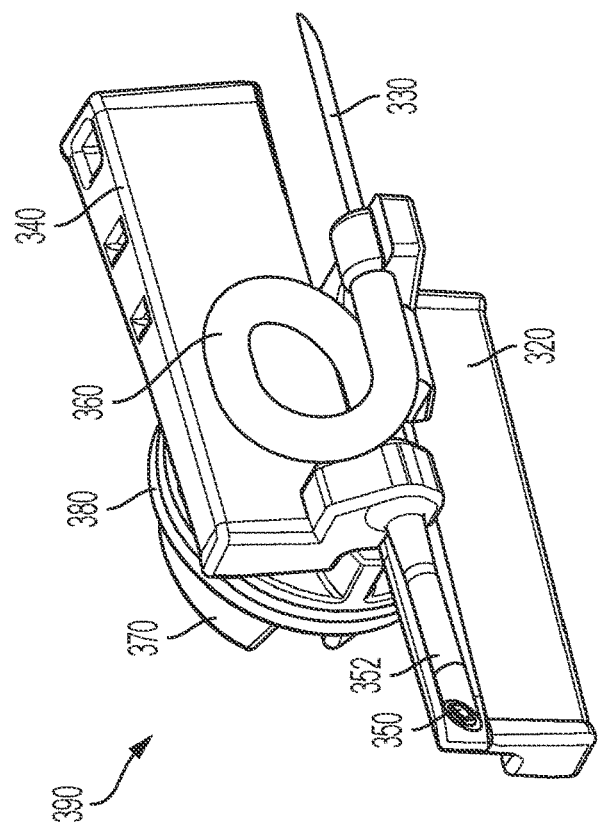
FIGS. 15 and 16 are perspective views of a needle mechanism within the needle assembly of FIG. 11.
Figure 15:
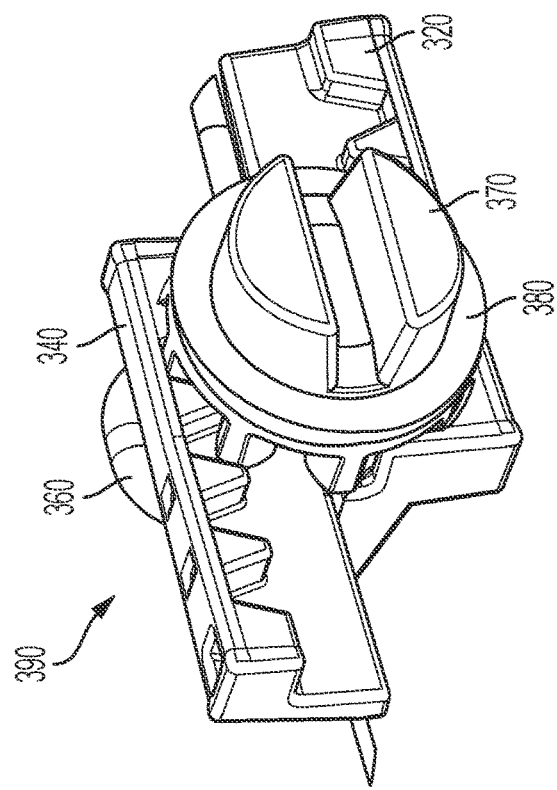
Figure 18:
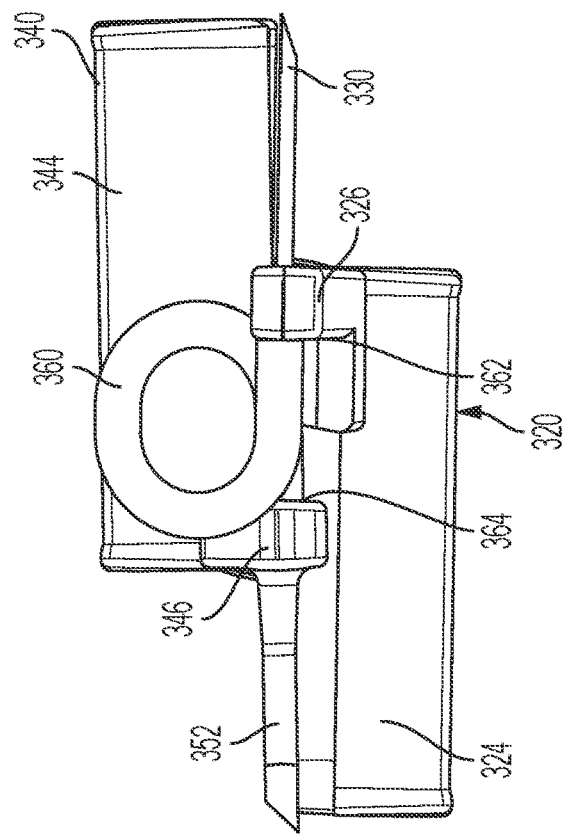
FIGS. 17 and 18 are side elevational views of the needle mechanism of FIGS. 15 and 16 without the driving member.

In the illustrated embodiment, needle assembly 300 is configured to interact with the patient's skin for delivery of the above-described medication. A first or distal end 392 of needle assembly 300 is positioned against the skin, and a second or proximal end 394 of needle assembly 300 interacts with cartridge 130. The needle assembly 300 is configured to couple to cartridge 130 either directly, or through needle assembly coupler 210. The first end 392 and/or the exterior seal 395 may comprise an adhesive to assist in positioning the needle assembly 300 against the patient's skin and may also comprise fasteners or adhesives to secure the needle assembly 300 to cartridge 130. As shown in FIG. 14, the internal housing 312 is supported by the housing 310, and the needle mechanism 390 is supported by the internal housing 312. In other embodiments, needle assembly 300 may comprise only one housing, and internal housing 312 may be integral to assembly housing 310.

Referring to FIGS. 14, the needle mechanism 390 is configured to fit entirely within needle assembly 300 when in a first configuration. FIGS. 14-18 show various views of needle mechanism 390 in the first configuration. In the first configuration, first needle 330 and second needle 350 are approximately aligned parallel to one another in the direction of central axis A1. As shown, first needle 330 and second needle 350 are pointed in approximately opposite directions along axis A1. First needle 330 is pointed towards first end 392 of needle assembly 300, and second needle 350 is pointed towards second end 394 of needle assembly 300.

As will be described later, first needle 330 and second needle 350 are configured to move generally along axis A1 when the needle assembly 300 is activated.

Figure 20:
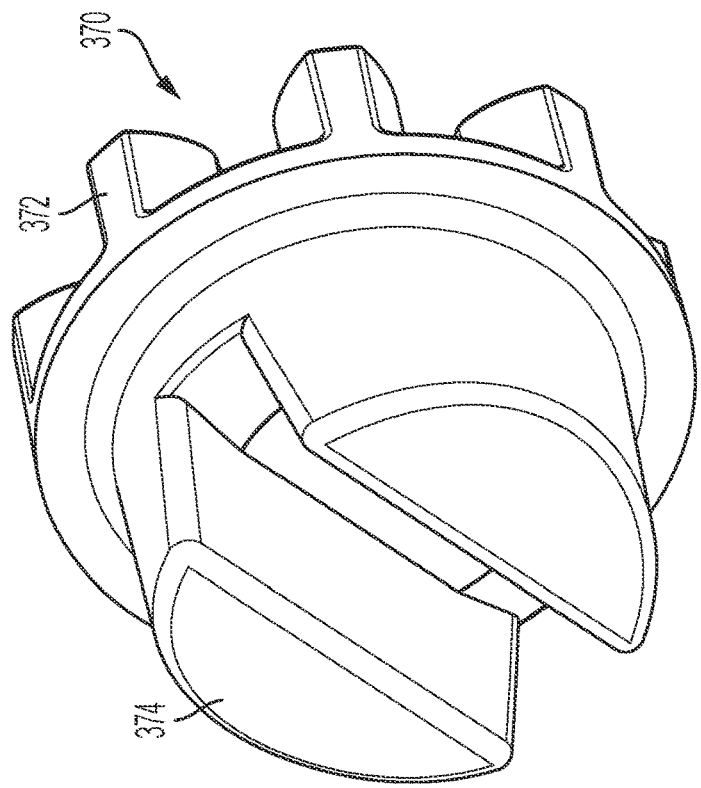
FIGS. 19 and 20 are perspective views of a driving member of the needle mechanism of FIGS. 15 and 16.

Referring to FIGS. 15-18, an exemplary embodiment of needle mechanism 390 is shown. First needle support 320 and second needle support 340 are positioned generally along a common plane and are slidably coupled to one another through driving member 370. A first side of first and second needle supports 320, 340 is configured to interact with driving member 370, and a second side of first and second needle supports 320, 340 is configured to interact with and support first and second needles 330, 350. In the illustrated embodiment, first and second needle supports 320, 340 are generally rectangular in shape and are configured to fit within needle assembly 300, as shown in FIG. 20. In other embodiments, first and second needle supports 320, 340 may be any shape to accommodate motion of needles 330, 350 and fit within needle assembly 300. In the illustrated embodiment, needle mechanism 390 comprises a rack and pinion configuration, wherein each of first needle support 320 and second needle support 340 is a rack, and driving member 370 includes a pinion gear. First needle support 320 comprises a support body 324, support engagement features 322, and a needle retainer 326. The needle retainer 326 is configured to couple with first needle 330 by inserting at least of portion of first needle 330 into needle retainer 326, thereby coupling first needle 330 to first needle support 320. Similarly, second needle support 340 comprises a support body 344, support engagement features 342, and a needle retainer 346, and the second needle 350 is coupled to second needle support 340 through needle retainer 346. As shown best in FIGS. 16 and 18, one or both of first needle support 320 and second needle support 340 may additionally comprise a needle guard 352, which may function to protect the needle and/or to provide additional strength to the needle. The illustrative needle guard 352 is a cylindrical housing with a bore extending therein, through which the respective needle 330, 350 extends.

First needle 330 and second needle 350 are fluidly coupled to one another through movable connector 360. Movable connector 360 is configured to be movable relative to each of the needles 330 and 350. Movable connector 360 may be movable by flexing, bending, stretching, or otherwise deforming. Accordingly, movable connector 360 may be composed of a flexible material, such as an elastomer, thermoset polymer, or rubber. In an exemplary embodiment, movable connector 360 is composed of silicone. In another embodiment, movable connector 360 may be composed of rigid materials coupled together through flexible connections. In yet another embodiment, movable connector 360 may be formed of relatively rigid materials and may move through a telescoping action. In the illustrated embodiment of FIG. 24, movable connector 360 is a flexible tube having a first end 362 fluidly coupled to the end of the first needle 330 and a second end 364 fluidly coupled to the end of the second needle 350. The ends 362, 364 of the flexible tube of the movable connector 360 may be coupled directly to the needle ends 330, 350 or to the respective needle retainers 326, 346. As described further below, the ends 362, 364 of the flexible tube are configured to move with the needles 330, 350.

Figure 17:
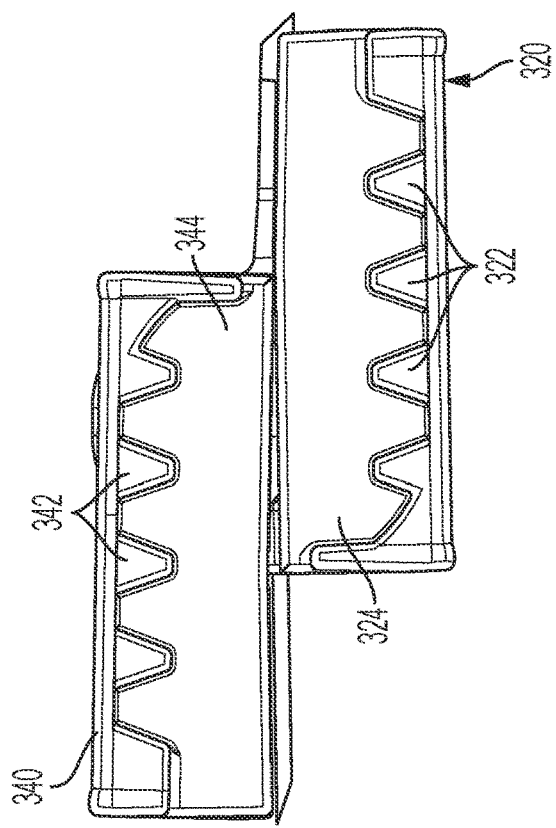
Figure 19:
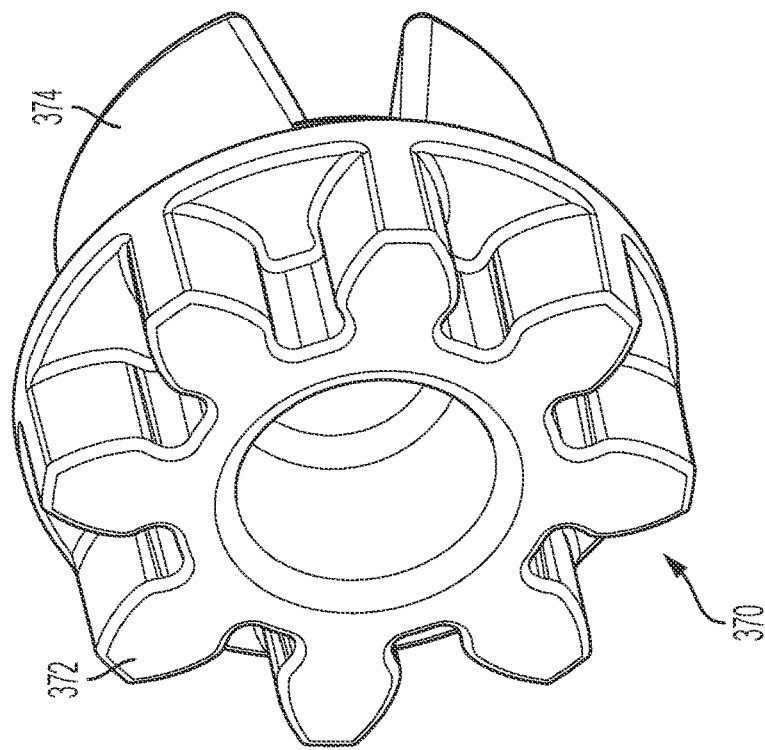

As shown best in FIGS. 19-20, driving member 370 comprises driving engagement features 372, and an actuating member 374. The O-ring 380 may be provided on driving member 370 in order to provide a better seal between driving member 370 and assembly housing 310, or to allow driving member 370 to rotate more easily within assembly housing 310. The driving engagement features 372 are configured to interact with the support engagement features 322 and 342 (FIG. 17). In the illustrated example, driving engagement features 372 and support engagement features 322 and 342 are teeth or protrusions configured to mesh together in a rack and pinion mechanism. In other embodiments, any of the engagement features within needle mechanism 390 may be other features configured to interact with one another such as protrusions and recessions, screws and threads, zipper type features, or any other complimentary engagement features. Furthermore, in the illustrated example, actuating member 374 is configured to be actuated by a rotation of a flat object, such as a flat-head screwdriver. In other embodiments, actuating member 374 may be actuated by an electric motor, a torsional spring, or human interaction such as rotation of a knob. In one exemplary embodiment, both the stopper driving system 120 and driving member 370 are each independently driven by an electric motor, such as first motor 22 and second motor 57 (FIG. 9). One electric motor may control the movement of both stopper driving system 120 and driving member 370, or they may each have their own respective actuating motors.

Figure 22:
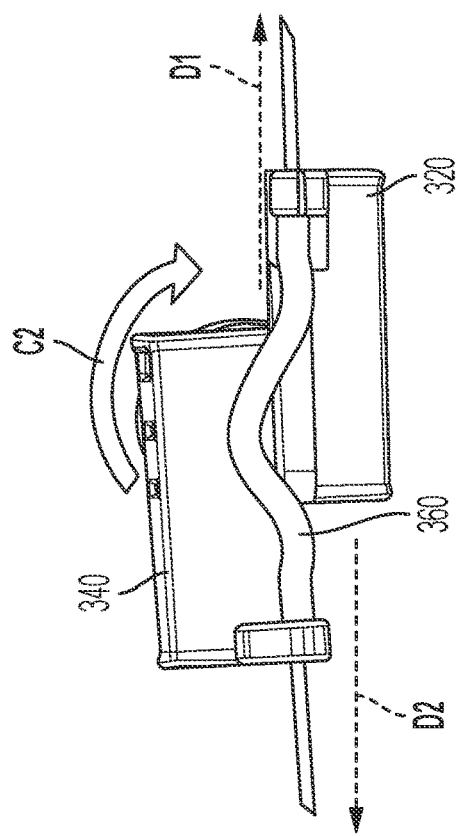
FIGS. 21 and 22 are side views of the needle mechanism of FIGS. 15 and 16 showing a motion of the needle mechanism from a first configuration in FIG. 21 to a second configuration in FIG. 22.
Figure 21:
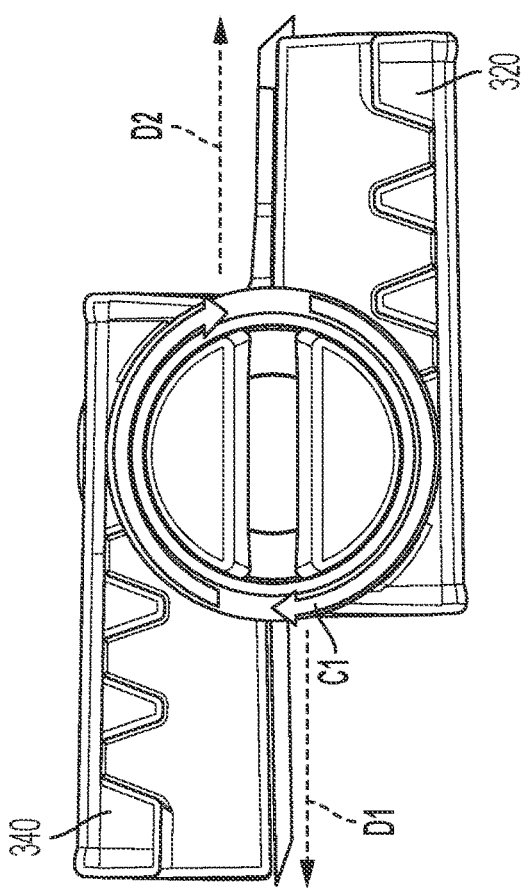

Referring now to FIGS. 21-22, the needle mechanism 390 is configured to allow for movement of first needle support 320 and second needle support 340 upon activation of driving member 370. Needle mechanism 390 is movable between a first, retracted configuration before use and/or after use, as shown in FIG. 21, and a second, extended configuration during use, as shown in FIG. 22. The needle mechanism can then return a third, retracted configuration after use to indicate to the patient that the injection is done and to hide the needle inside the assembly so that the patient does not need to see the needle or handle the needle when disposing the cassette.

In the first, retracted configuration of FIG. 21, both first needle 330 and second needle 350 are axially positioned entirely within assembly housing 310. Movable connector 360 may be arranged in a compressed (e.g., bent or looped) state between closely-positioned tube ends 362, 364 and needles 330, 350 in the first configuration, where the closely-positioned tube ends 362, 364 are separated by a first distance. Upon rotation of driving member 370 in a direction C1, first needle support 320 and first needle 330 are driven in a direction D1, and second needle support 340 and second needle 350 are driven in a direction D2 until the rotation of driving member 370 stops once the needle mechanism 390 is in the second configuration. In the illustrated embodiment, D1 and D2 are approximately parallel within a plane and are generally opposite of one another. Furthermore, they are approximately parallel to axis A1 (See FIG. 14). In other embodiments, D1 and D2 may be angled relative to one another, and may not be approximately parallel to A1.

In the second, extended configuration, first needle 330 extends axially beyond assembly housing 310 and passes through the outer seal 395 and into whatever surface needle assembly 300 is positioned against. Additionally, second needle 350 extends axially beyond assembly housing 310 and passes through interior seal 396 and septum 135 into fluid housing 131. Because the movable connector 360 is movable, it maintains fluid communication between first needle 330 and second needle 350 throughout movement of the needle mechanism 390. Movable connector 360 may be arranged in an extended state between the now-distant tube ends 362, 364 and needles 330, 350 in the second configuration, where the now-distant tube ends 362, 364 are separated by a second distance larger than the first distance of the first configuration. In the second configuration, first needle 330 is fluidly coupled to cartridge 130, so the medication within fluid housing 131 is capable of flowing through second needle 350, movable connector 360, and first needle 330 into whatever body or surface first needle 330 has pierced. In an exemplary embodiment, the stopper driving system 120 is activated after needle mechanism 390 is in the second configuration, and the medication within cartridge 130 is driven out and into the body or surface pierced by first needle 330. In another embodiment, a number of components of needle mechanism 390, and/or the internal housing 312 comprise a stopping feature to physically stop the movement of first needle support 320 and second needle support 340 once needle mechanism 390 reaches the second configuration. Such a stopping feature may be a blocking member, a protrusion, a detent, or an absence of engagement members within a portion of the needle mechanism 390.

From the second configuration, needle mechanism 390 is configured to be movable back to the first configuration through reverse activation of driving member 370 as well. As shown in FIG. 22, driving member 370 may be rotated in a direction C2, which is generally opposite to C1, in order to drive first needle support 320 in the direction D2, and second needle support 340 in the direction D1. In an exemplary embodiment, needle mechanism 390 is moved from the second configuration to the first configuration after the medication has been driven out of cartridge 130 and through needle mechanism 390. In an embodiment where cassette 100 is being used to deliver the above-described medication to the patient, extending the first needle 330 from needle assembly 300, and then retracting the first needle 330 back into the needle assembly 300 after injection would allow the patient to be injected with a medication without needing to directly observe or handle the first needle 330.

Figure 23:
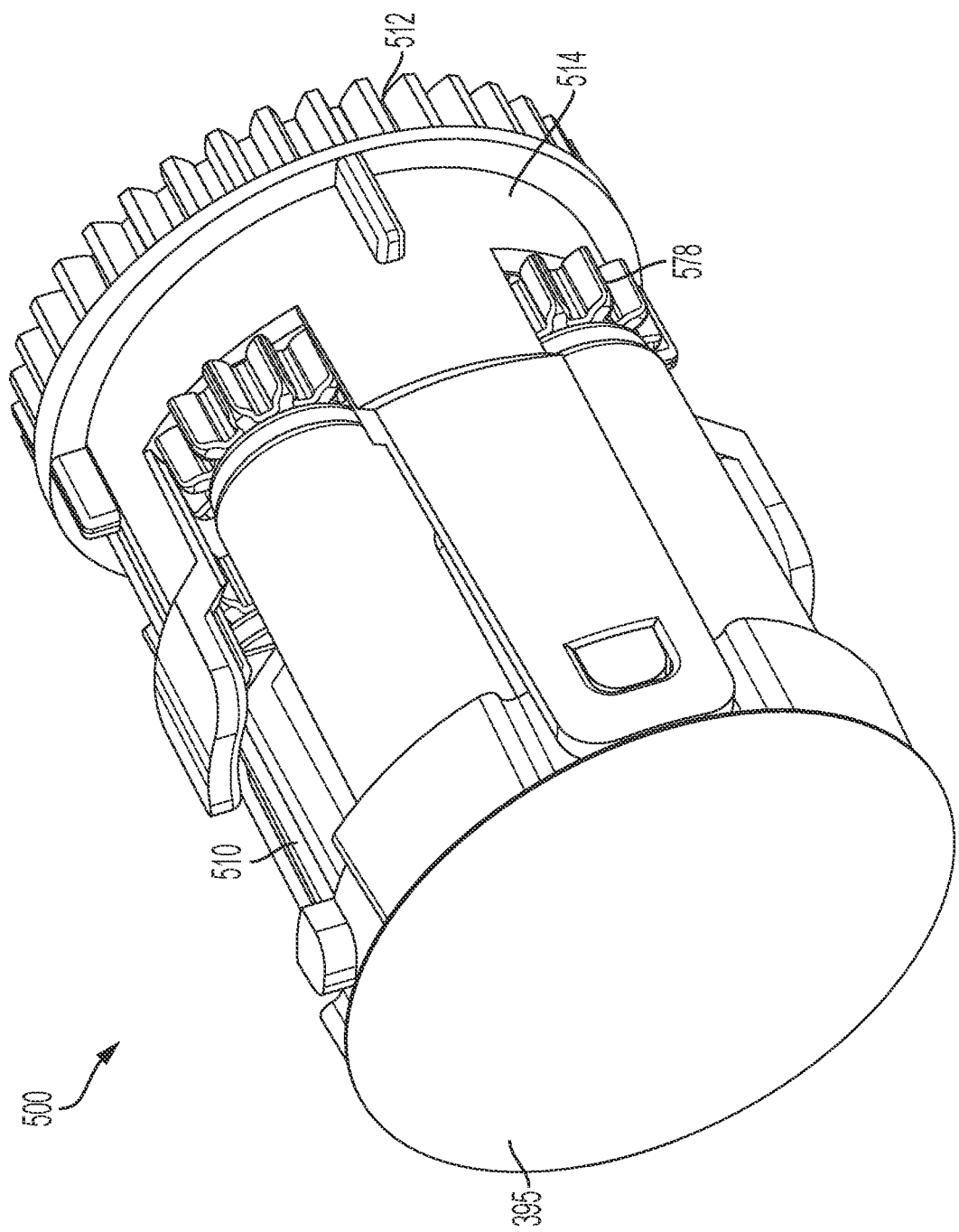
FIG. 23 is a perspective view of yet another embodiment of a needle assembly.
Figure 24:
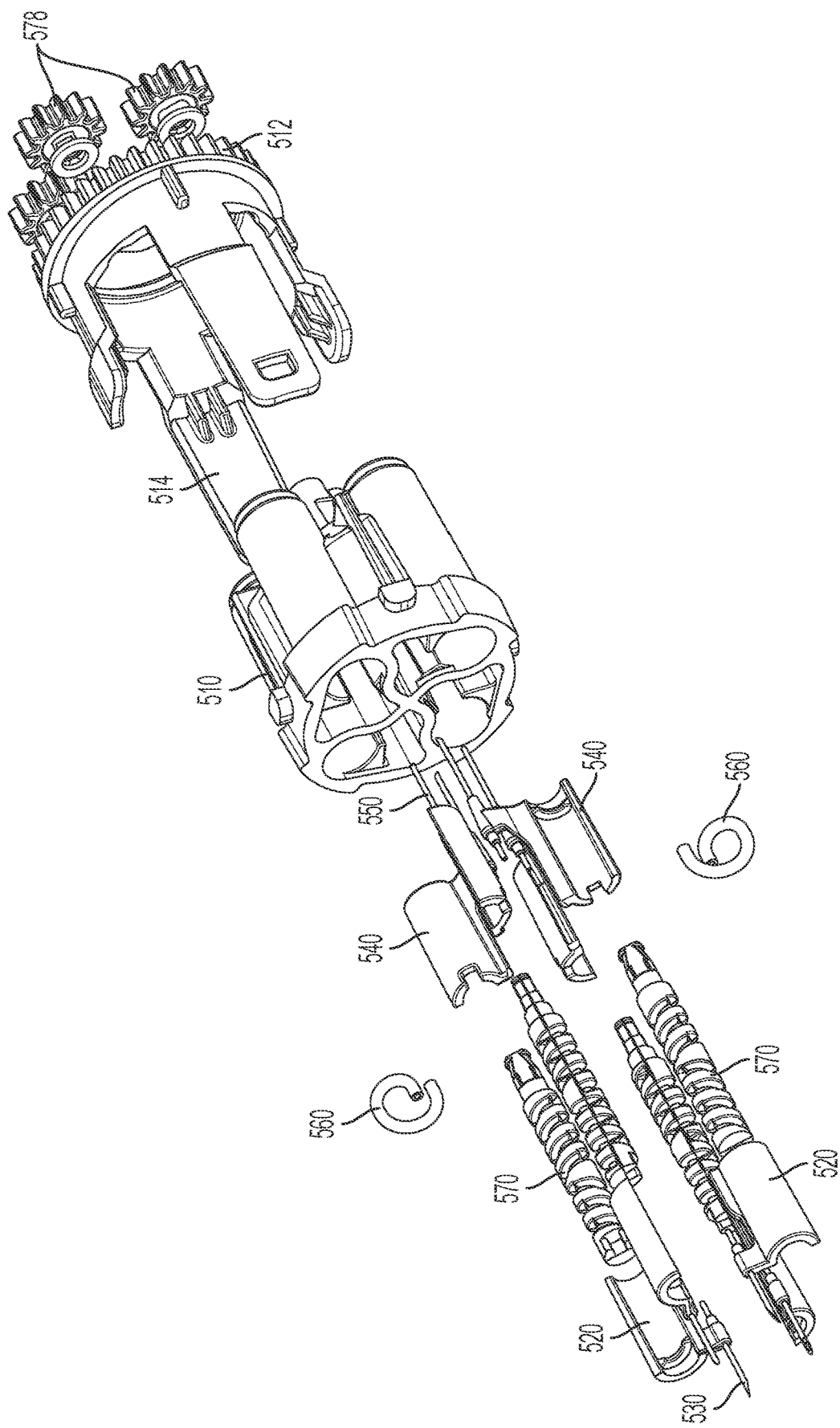
FIG. 24 is an exploded view of the needle assembly of FIG. 23.

Referring now to FIGS. 23-24, another embodiment of a needle assembly 500 is shown. Needle assembly 500 comprises a housing 510, a rotating assembly 514, and a plurality of needle mechanisms 590. Each needle mechanism 590 comprises a first needle support 520 coupled to a first needle 530, a second needle support 540 coupled to a second needle 550, a movable connector 560, a driving member 570, a driving member actuator 578, and an O-ring 580. In the illustrated embodiments, a plurality of needle mechanisms 590 are shown, but any number of needle mechanisms 590 may be used, including a single needle mechanism 590, similar to the embodiment shown in FIG. 11. Movable connector 560 may have various features in common with the above-described movable connector 360.

Rotating assembly 514 comprises an exposed driven gear 512 and is configured to couple with housing 510. In an exemplary embodiment, driven gear 512 is driven by a motor to rotate housing 510 through rotating assembly 514. In other embodiments, rotating assembly 514 may not comprise driven gear 512, and may instead have a different feature to facilitate its rotation, such as a grip to be rotated by a user, or other engagement features to be rotated by a motor or another device. In still other embodiments, rotating assembly 514 may be configured to only rotate the needle mechanisms 590 within housing 510 instead of rotating the entire needle assembly 500.

Referring now to FIGS. 25-28, the needle mechanisms 590 of needle assembly 500 are configured as a drive screw assembly. Each of the first needle support 520 and the second needle support 540 comprise an engagement feature 522, a support body 524, and a needle retainer 526. The first needle support 520 and second needle support 540 are configured to engage with driving member 570. Each of first and second needle supports 520, 540 is generally curved to accommodate interaction with driving member 570 and is configured to position first and second needles 530, 550 generally proximate one another. In other embodiments, first and second needle supports 520, 540 may be configured to position first and second needles 530, 550 on opposite sides of a central axis from one another. Each engagement feature 522 is configured to interact with a driving engagement feature 572 of driving member 570. In the illustrated embodiments, engagement feature 522 is in threaded engagement with the driving member 570. Engagement feature 522 is shown as a thread, driving member 570 is shown as a threaded shaft such as a screw, and driving engagement feature 572 is a trough or root within the screw. The engagement feature 522 is configured to be received within or otherwise interact with the driving engagement feature 572 of driving member 570. In the illustrated embodiment, driving engagement features 572 of driving member 570 are oppositely oriented along opposing halves of driving member 570 such that rotation of driving member 570 causes opposite axial movement of first and second needle supports 520, 540. A driving gear 578 is coupled to each driving member 570 such that rotation of driving member actuator 578 causes rotation of driving member 570. Driving member 570 also comprises at least one stopping feature 573 configured to stop a movement of first needle support 520 and/or second needle support 540 along driving member 570. In the illustrated embodiment, driving member 570 comprises a stopping feature 573 on each half of driving member 570.

Figure 28:
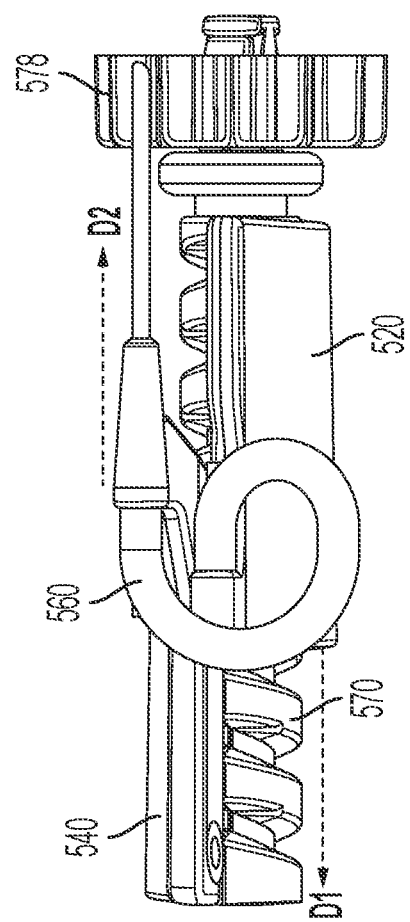
FIG. 28 is a side view of a needle mechanism within the needle assembly of FIG. 23 showing a movement of the needle mechanism from a first configuration in FIG. 38.

Referring now to FIG. 28, the needle mechanisms 590 may be extended and retracted similarly to the needle mechanisms 390, but through the use of a different driving mechanism. More specifically, the needle mechanisms 590 may be moved between a first, retracted configuration before use and/or after use, as shown in FIG. 38, and a second, extended configuration during use (not shown). Within a needle mechanism 590 of needle assembly 500, the driving member actuator 578 is rotatable locked with the driving member 570, and thus when rotated, the rotation of driving member 570 is caused. The engagement feature 522 on first needle support 520 and second needle support 540 are configured to move first needle support 520 and second needle support 540 in opposite axial directions along driving member 570 when driving member 570 is rotated. Each needle mechanism 590 begins in the first configuration, as shown in FIG. 38, and rotation of driving member 570 in a first direction causes first needle support 520 to move in the direction D1, and second needle support 540 to move in the direction D2, thereby moving the needle mechanism 590 into the second configuration. The driving of member actuator 578 stops the movement of first needle support 520 and second needle support 540 once the needle mechanism 590 reaches the second configuration. The driving member 570 may then rotate in a second, opposite direction to move the needle mechanism 590 from the second configuration to the first configuration by moving first needle support 520 in the direction D2, and second needle support 540 in the direction D1. All previous disclosure related to the first configuration, second configuration, needles, uses, etc. as discussed regarding needle assembly 300 may be applied to needle assembly 500. Utilizing a screw mechanism as in needle assembly 500 may allow needle assembly 500 to occupy less space than rack and pinion mechanisms as in needle assembly 300 and needle assembly 400.

One or more benefits can be realized with any of the cassette with any of needle mechanisms disclosed herein being movable between the first and second configurations where the fluid path between the medication reservoir and the needle injecting into the patient is created (first configuration) and removed (second configuration), that is the fluid path between the medication reservoir and the needle injecting into the patient is decoupled. One benefit of this decoupling may be that the dose delivery accuracy may be potentially improved because of the absence of drool from the plunger decompressing (which can maintain a slight internal pressure). This can result in reduced hold time of the device at the treatment site by the patient to achieve dose accuracy. One or more of the benefits for gearing mechanisms and needle supports described herein is having very tightly guided needle movement. Accordingly, such tightly guided control can more effectively hitting a small septum target and/or pushing the needle straight in and out of the patient skin (less likely to hit a proximal nerve).

Figure 25:
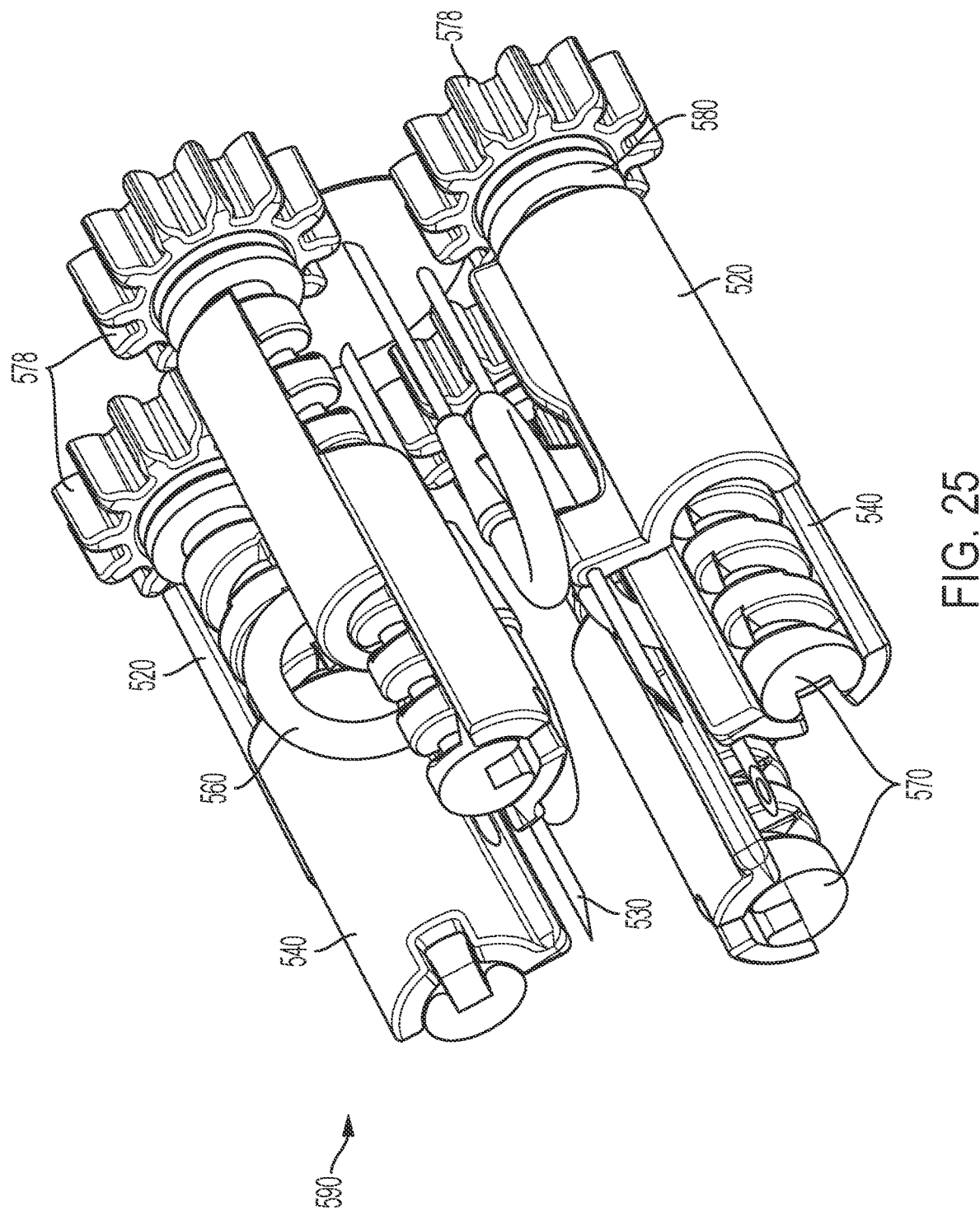
FIG. 25 is a perspective view of a needle mechanism within the needle assembly of FIG. 23.
Figure 27:
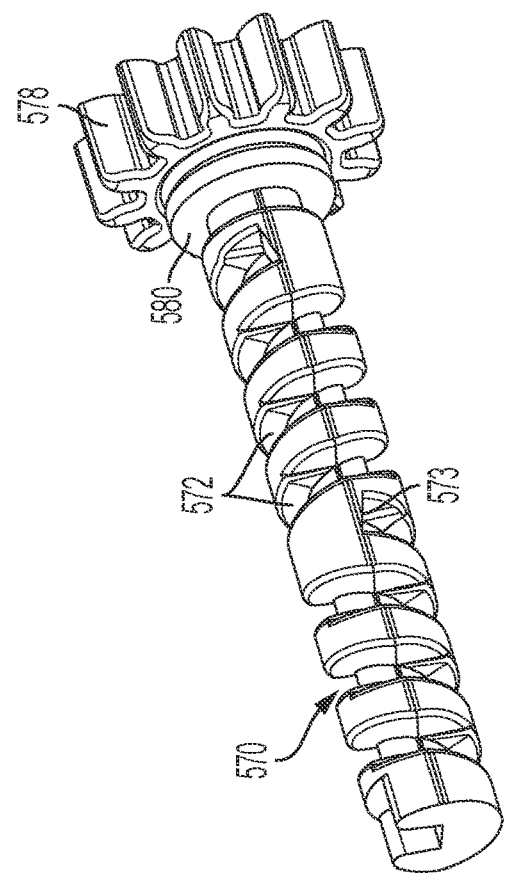
FIG. 27 is a perspective view of a driving member of the needle mechanism of FIG. 25.
Figure 26:
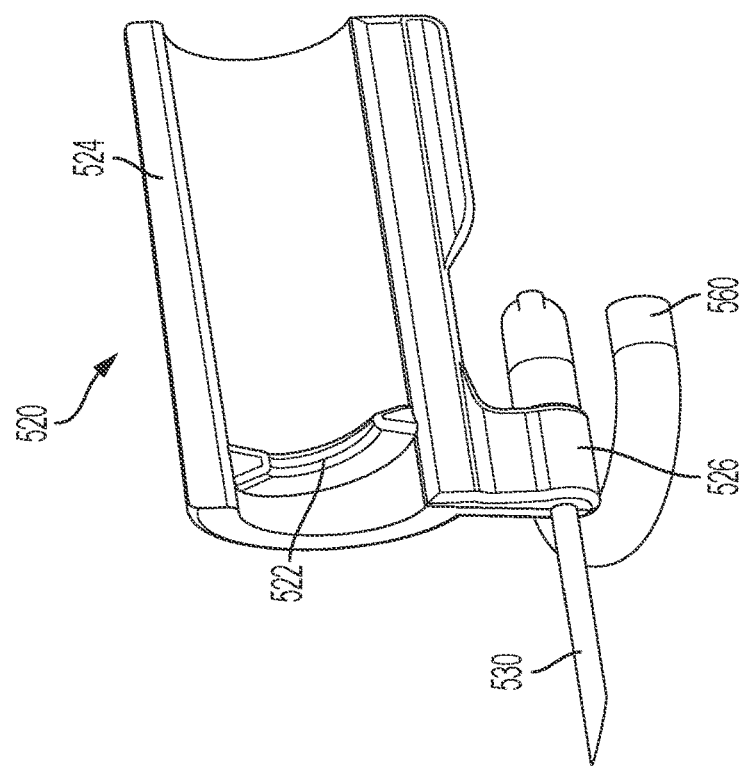
FIG. 26 is a perspective view of a needle support of the needle mechanism of FIG. 25.

As shown in FIG. 25, multiple needle assemblies may be used. Additional details regarding the use of multiple needle assemblies, as well as needle assemblies which may be operated with two needles oriented along different axis (e.g. perpendicular needles), may be found in the above-incorporated U.S. Provisional Application No. 63/126,552.

Figure 30:
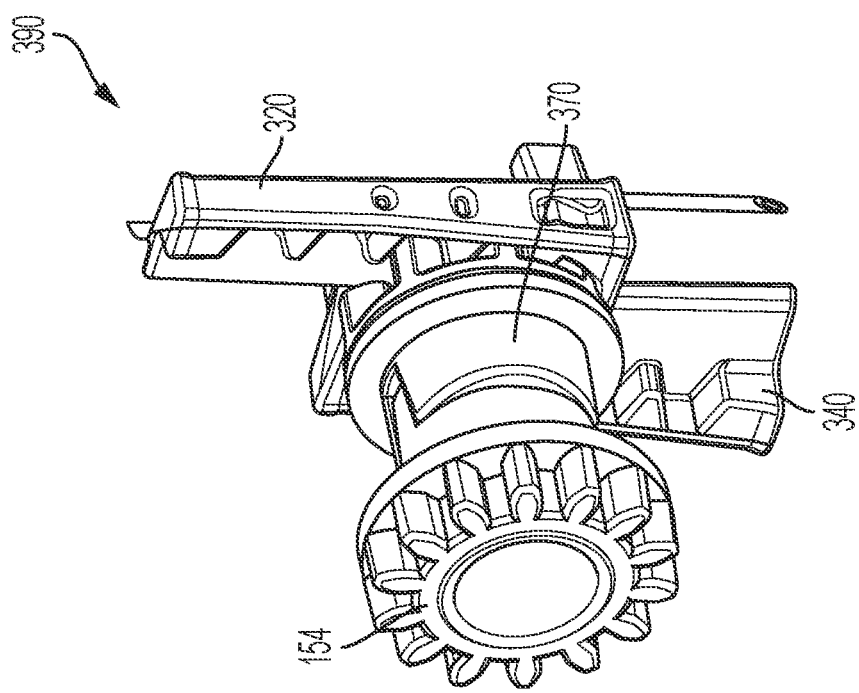
FIGS. 29 and 30 are perspective views of a needle mechanism within the device of FIG. 4.
Figure 29:
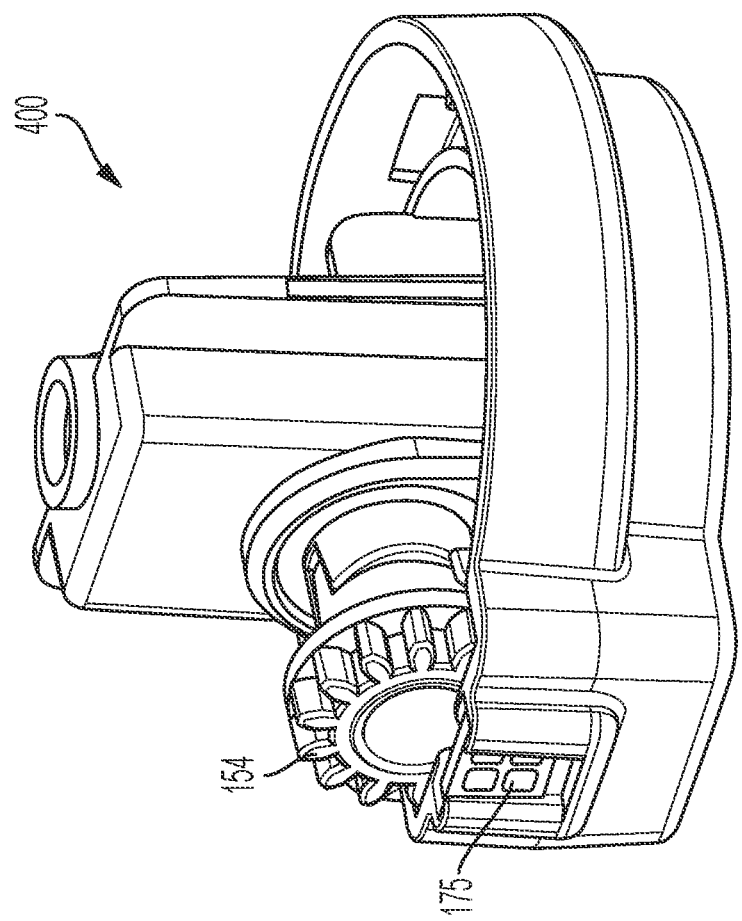

Referring now to FIGS. 29-30, needle assembly 400 is shown configured to be used with needle mechanism 390. Needle assembly 400 may comprise similar features to needle assembly 300 as described above. Assembly 400 may have a lower tubular body and an intermediate portion extending axially from the lower tubular body. The lower tubular body may define a radial recess in which the gear 154 resides (the face of gear facing radially outward). The rotating axis of gear 154 may be perpendicular to the central axis, as shown in the figures. The intermediate portion forms an enclosure about the needle mechanism 390. The intermediate portion may include a radial opening in which a shaft from gear 154 extends radially inward into the intermediate portion. The intermediate portion may include an opening in which the needle from needle mechanism 390 selectively extends therethrough. Needle assembly actuating gear 154 is configured to actuate driving member 370 and thereby activate needle mechanisms 390. As described above, actuating gear 154 may be actuated by a motor within a reusable housing, or manually by a user.

Figure 32:
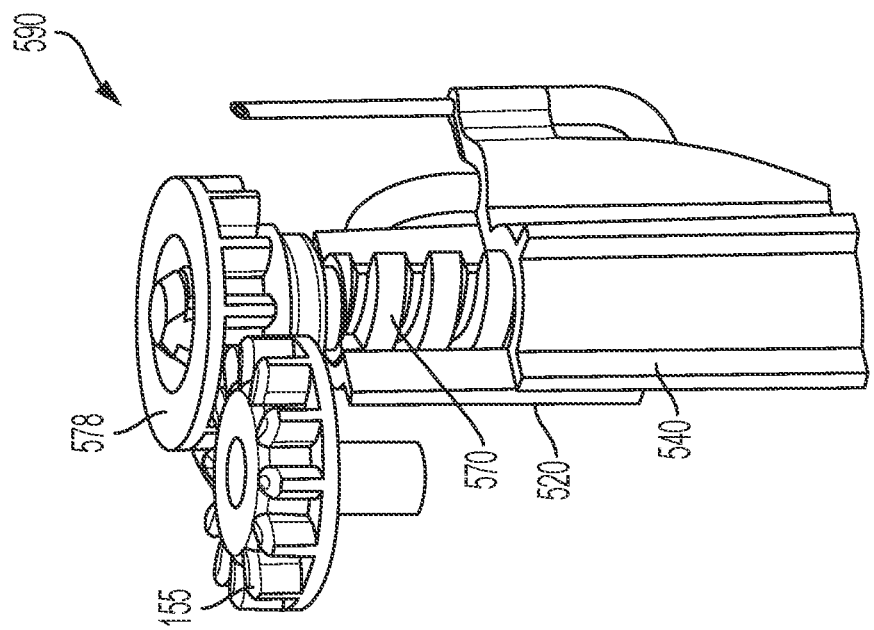
FIGS. 31-32 are perspective views of another needle mechanism within the device of FIG. 4.
Figure 31:
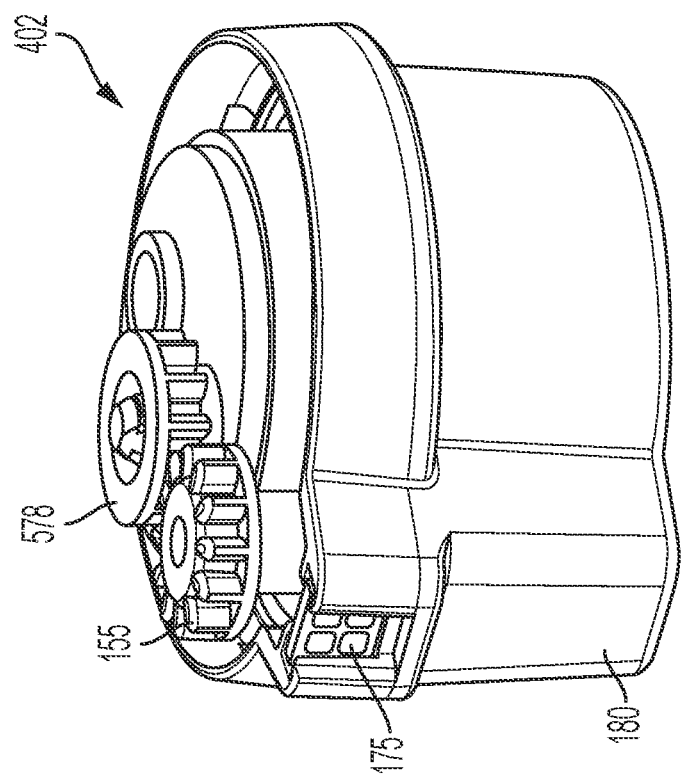

Referring now to FIGS. 31-32, needle assembly 402 is shown configured to be used with needle mechanism 590. Needle assembly 402 may comprise similar features to needle assembly 500 as described above. Needle assembly actuating gear 155 is configured to mesh with and rotate driving member actuator 578, thereby actuating driving member 570 and actuating needle mechanisms 590. Assembly 402 may have a lower tubular body and an intermediate portion extending axially from the lower tubular body. The lower tubular body may define a recess in which the shaft of gear 155 resides (face of gear facing axially). The intermediate portion forms an enclosure about the needle mechanism 590. The intermediate portion may include a first axial opening in which driving member 570 extends therethrough. Driving member actuator 578 is rotationally fixed to the driving member 570 and is drivably engaged with gear 155. The intermediate portion may include another axial opening in which the needle from needle mechanism 590 selectively extends therein.

Figure 33:
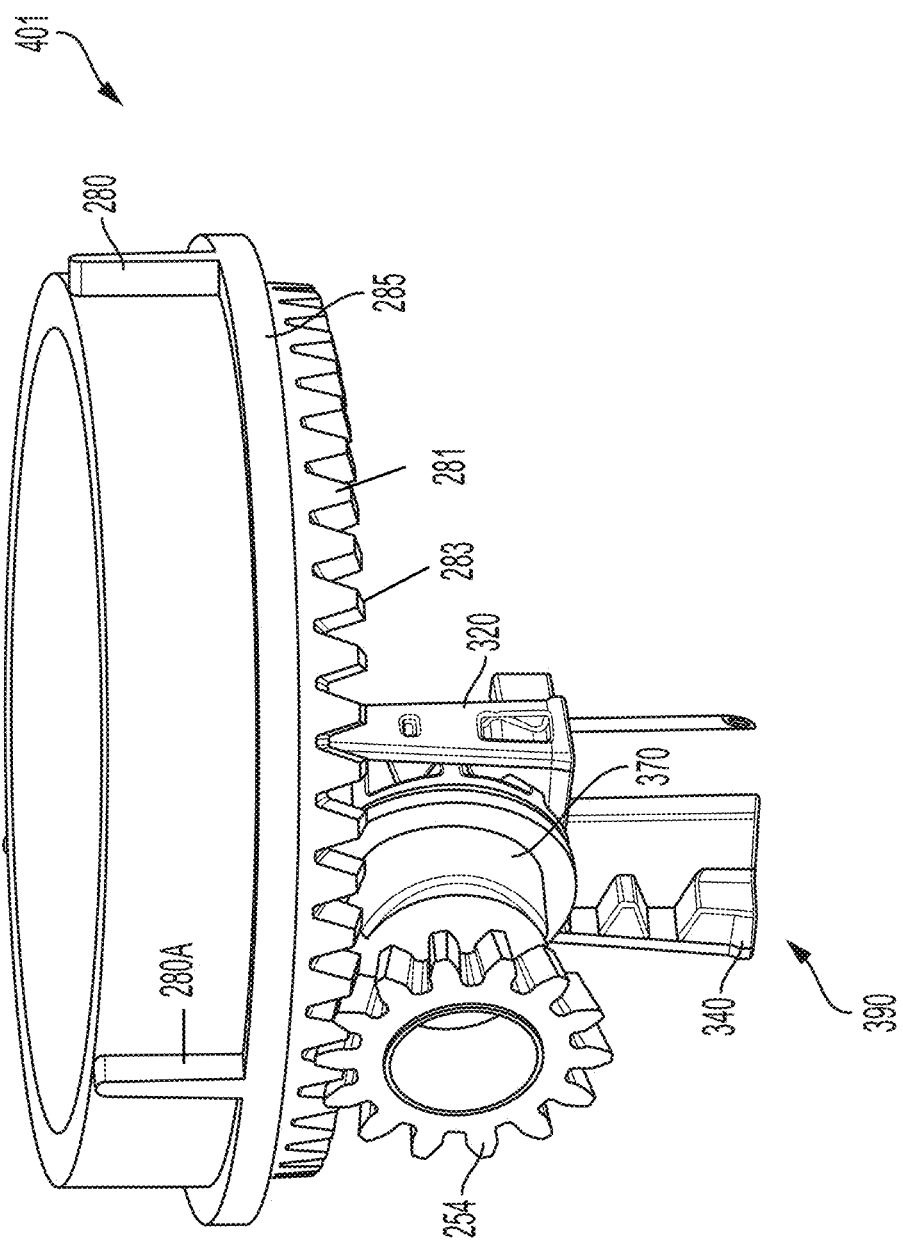
FIGS. 33-34 are perspective views of a needle mechanism within the device of FIG. 6.

Referring to FIG. 33, needle assembly 401 is shown without a needle assembly housing. Needle assembly 401 is configured to be used with needle mechanism 390. Needle assembly 401 may comprises similar features to needle assembly 300 as described above. Needle assembly actuating gear 254 is configured to actuate driving member 370 thereby activating needle mechanisms 390. Gear 254 can be driven by external gear 280. Gear 280 can be formed in a ring shape with gear driving teeth 281 formed along an edge 283 of its body for axial engagement with the gear 254. External gear 280 may include at least a partially circumferential radial lip 285 extending from the outer surface of the gear 280 that is slidably engaged with the upper edge of the lower portion 410 (as shown in FIG. 7). External gear may include one or more driven teeth or gear interfacing features 280A that are driven by the motor or user. The driven teeth 280A may be circumferentially spaced from one another along the outer surface. In one embodiment, the driven teeth 280A are shown as axially extending protrusions extending away from the radial lip 285. The gear interfacing features 280A may include recesses instead of protrusions. As external gear 280 rotates, being driven, for example, by second motor, the gear driving teeth drivably engage the teeth of gear 254 thereby moving the needles as described above, for example, with reference to FIGS. 21-22.

Figure 34:
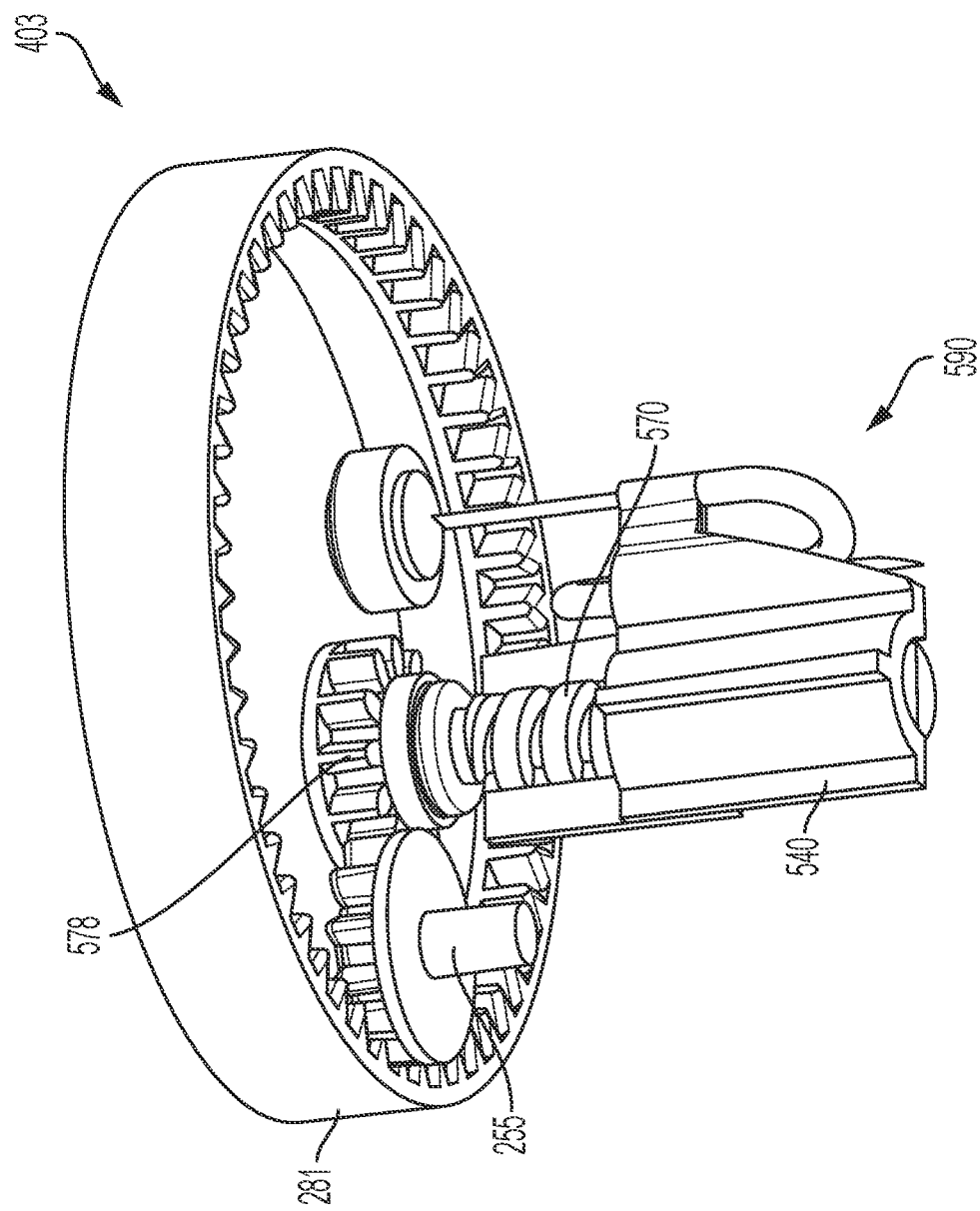

Referring now to FIGS. 34, needle assembly 403 is shown configured to be used with needle mechanism 590. Needle assembly 403 may comprise similar features to needle assembly 500 as described above. Needle assembly actuating gear 255 is configured to mesh with and rotate driving member actuator 578, thereby actuating driving member 570 and actuating needle mechanisms 590. The rotating axis of the gear 255 may be offset and parallel with the central axis, as shown in the figures. The rotating axis of the gear 578 may be offset and parallel with the central axis, and offset from the rotating axis of gear 255, as shown in the figures. Gear 255 can be driven by external gear 281. Gear 281 is formed in a ring shape with gear teeth formed radially inward facing along an edge of its body for radial engagement with the gear 255. In one embodiment, the driven teeth or external gear interface features are disposed circumferentially spaced from one another around the axis (not shown) may be axially extending protrusions along the outer surface, similar to gear 280. As external gear 281 rotates, being driven, for example, by second motor, the gear driving teeth drivably engage the teeth of gear 255 that drivably engages the teeth of the driving member actuator 578 thereby moving the needles as described above.

Figure 35:
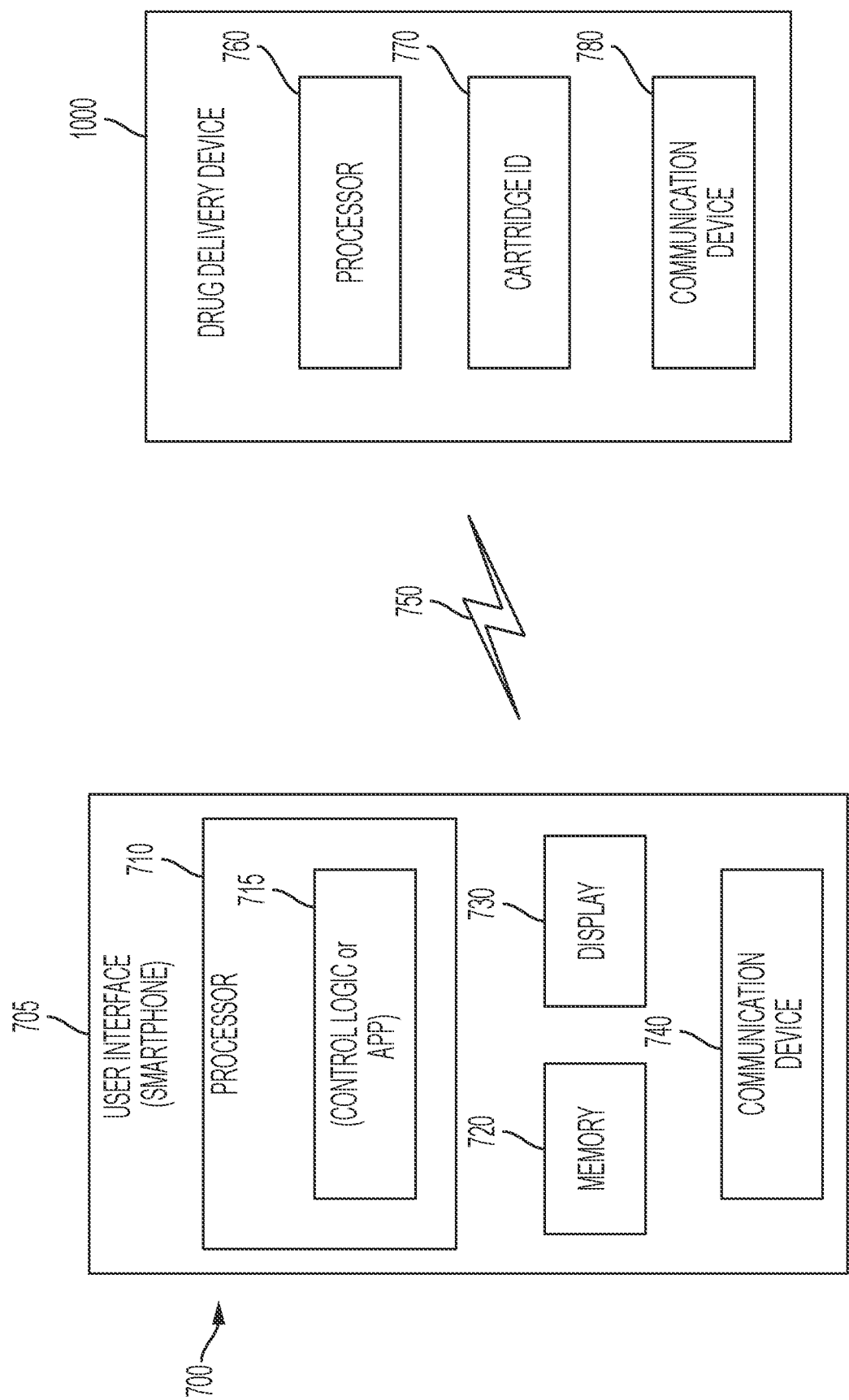
FIG. 35 is diagrammatic view of an exemplary wireless communication system for use with a drug delivery device.

Referring now to FIG. 35, a computing device 700 may be used to communicate with and/or operate any of the drug delivery devices 11, 12, 13, 100 described herein, illustratively cassette 100. Computing device 700 illustratively includes a mobile device, such as a smartphone. Alternatively, any suitable computing device may be used, including but not limited to a laptop, desktop, tablet, or server computer, for example.

The computing device 700 includes at least one processor 710 that executes software and/or firmware stored in memory 720 of device 700. The software/firmware code contains instructions that, when executed by processor 710, causes device 700 to perform the functions described herein. The at least one processor 710 illustratively includes control logic and/or an application 715 operative to activate cassette 100. Memory 720 is any suitable computer readable medium that is accessible by processor 710. Memory 720 may be a single storage device or multiple storage devices, may be located internally or externally to processor 710, and may include both volatile and non-volatile media. Exemplary memory 720 includes random-access memory (RAM), read-only memory (ROM), electrically erasable programmable ROM (EEPROM), flash memory, a magnetic storage device, optical disk storage, or any other suitable medium which is configured to store data and which is accessible by processor 710.

Computing device 700 includes a user interface 705 in communication with processor 710 and operative to provide user input data to the system and to receive and display data, information, and prompts generated by the system. User interface 705 includes at least one input device for receiving user input and providing the user input to the system. In the illustrated embodiment, user interface 705 is a graphical user interface (GUI) including a touchscreen display operative to display data and receive user inputs. The touchscreen display allows the user to interact with presented information, menus, buttons, and other data to receive information from the system and to provide user input into the system. Alternatively, a keyboard, keypad, microphone, mouse pointer, or other suitable user input device may be provided.

Computing device communicates with cassette 100 through signal 750. Signal 750 may be a wireless or wired signal. Cassette 100 may comprise a processor 760 similar to processor 710, a cassette ID 770, and/or a communication device 780. Communication device 780 may send or receive a signal 750 to/from communication device 740, or to/from other components of cassette 100 (e.g. cassette ID 770). cassette ID 770 may be any sort of mechanism or device that provides data about a component of cassette 100. For example, cassette ID 770 may be a chip or RFID indicator on cassette 100 (FIG. 12) that provides data regarding the type of liquid or medication within cartridge 130 (e.g. specific medication, viscosity, volume, dosage, injection scheduling, etc.). Other components, such as a needle assembly or motor, may include an ID to communicate other data related to cassette 100 (e.g. needle assembly type, needle length/positioning, patient information, historical treatment information, motor type, motor characteristics, etc.).

In some embodiments, cassette 100 may comprise an indicator (not shown) that provides some sort of indication that the medication has been delivered to the patient. Such an indication may be an end of dose indication. The indicator may comprise, for example, a light (e.g. an LED), a visual display such as a screen, a vibration, a sound, the sending of a signal, an indication on a separate computing device (e.g. a smartphone or computer as discussed above), a mechanical visual indicator (e.g. a window in the device housing to show barrel movement), or any combination thereof. The indicator may also indicate to a user any other information about the operation of cassette 100 including, but not limited to, whether or not a cassette is inserted, whether a cassette is inserted properly, device power information (e.g. whether the device is on/off, battery level), patient information, any information that may be provided by ID's discussed above, or any combination thereof.

In some embodiments, cassette 100 may comprise a number of sensors (not shown) that sense information related to the device. In an exemplary embodiment, cassette 100 comprises a skin sensor which senses whether the device is properly positioned against a patient's skin. In some embodiments, the cassette 100 may not actuate a needle assembly or deliver a medication if the skin sensor does not indicate that the device is positioned properly. Other examples of optional sensors include, but are not limited to, a medication level sensor, a pressure sensor, accelerometers, a force/thrust sensor, a position sensor for elements of the driving system, cartridge, housing, and/or needle assembly, a pH sensor, or any combination thereof. A temperature sensor may be provided to sense ambient temperature, medication temperature, or another component's temperature, and can be embodied, such as but not limited to a thermistor (e.g., a negative temperature coefficient (NTC) thermistor or a resistance temperature detector (RTD)), a thermocouple, or a semiconductor-based temperature sensor.

In some embodiments, the cassettes disclosed herein do not include the stopper drive systems 120, 220. Instead, the driving system of the housing of reusable portion is configured to engage with the stopper.

Some or all of the components of drug delivery devices disclosed herein, such as devices 11, 12, 13, 100, and 200 may be composed of a polymer or a disposable material. For example, some or all of the components of the drug delivery devices 11, 12, 13, and/or cassettes 100, and 200 may be composed of a cyclic olefin polymer. Additionally, some or all of the components of cassette 100 may be manufactured through additive manufacturing, extrusion, reductive machining, casting, molding, or any other suitable manufacturing process. In some embodiments, the housing, cartridge, fluid housing, orientation mechanism, driving system, and/or needle assemblies may be composed partially or entirely of a polymer. Producing certain components from a polymer may provide improved manufacturing tolerances compared to other materials such as glass, and may also reduce the impact of disposing of such devices or components.

The terms "first", "second", "third" and the like, whether used in the description or in the claims, are provided for distinguishing between similar elements and not necessarily for describing a sequential or chronological order. It is to be understood that the terms so used are interchangeable under appropriate circumstances (unless clearly disclosed otherwise) and that the embodiments of the disclosure described herein are capable of operation in other sequences and/or arrangements than are described or illustrated herein.

While this invention has been described as having exemplary designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

Various aspects are described in the description in this disclosure, which include, but are not limited to, the following aspects:

1. A drug delivery device including: a cassette comprising: a cartridge configured to retain a volume of a medication; a stopper driving system configured to drive the medication from the cartridge, the stopper driving system comprising a stopper, wherein the stopper travels less than 10 mm to deliver a volume of 1 mL of the medication; and a needle assembly directly coupled to the cartridge movable between an extended configuration and a retracted configuration, the needle assembly having an actuating gear movable between first and second positions, wherein in the extended configuration the actuating gear is in the second position and the needle assembly provides fluid communication between the cartridge and the needle assembly, wherein in the retracted configuration the actuating gear is in the first position and no fluid communication is provided between the cartridge and the needle assembly.

2. The drug delivery device of aspect 1, further including a reusable housing configured to receive the cassette and including a driving system, wherein the driving system is configured to operatively couple to at least the stopper driving system.
3. The drug delivery device of aspect 2, further including an orientation mechanism configured to orient the cartridge relative to the reusable housing when the cartridge is coupled to the reusable housing.
4. The drug delivery device of aspect 3, wherein the orientation mechanism includes a protrusion and the reusable housing includes a slot configured to receive the protrusion.
5. The drug delivery device of aspect 2, wherein the reusable housing is configured to receive the cassette at any rotational position around a central axis of the cassette.
6. The drug delivery device of any one of aspects 1-5, further including a first motor configured to actuate the stopper driving system to deliver the medication from the cartridge.
7. The drug delivery device of aspect 6, further including a second motor configured to actuate the actuating gear of the needle assembly.
8. The drug delivery device of any one of aspects 1-7, wherein the cassette has a height from 40 mm to 60 mm and a diameter from 20 mm to 40 mm.
9. The drug delivery device of any one of aspects 1-8, further including a cartridge ID coupled to the cartridge.
10. The drug delivery device of aspect 9, wherein the cartridge ID includes at least one circular ID, the circular ID configured to be read from a plurality of rotational orientations relative to a central axis of the circular ID.
11. The drug delivery device of aspect 9, wherein the cartridge ID includes at least one of an RFID indicator, a readable chip, and an antenna.
12. The drug delivery device of any one of aspects 1-11, wherein the cartridge, and at least a portion of the stopper driving system and the needle assembly are composed of a polymer.
13. A method of delivering a medication to a patient including: coupling a housing of a drug delivery device to a cassette with a needle assembly including a first needle and a second needle, wherein the needle assembly is in a retracted configuration where there is no fluid communication provided between the cartridge and the needle assembly; orienting the housing relative to the cassette; positioning the drug delivery device against a skin of the patient; actuating the needle assembly of the drug delivery device to extend the first needle into the skin of the patient and the second needle into a septum of a cartridge containing a volume of a medication; actuating a driving system to drive a stopper to travel less than 10 mm for a 1 mL volume of the medication from the cartridge through the needle assembly and to the patient; and retracting the first and second needles within the needle assembly, where there is no fluid communication provided between the cartridge and the needle assembly.
14. The method of aspect 13, wherein the orienting step is carried out through an orientation mechanism.
15. The method of aspect 14, wherein the orientation mechanism includes at least one of a protrusion, a slot, and a gear.

16. The method of any one of aspects 13-15, further including the step of decoupling the housing from the cassette after the retracting step.

17. The method of any one of aspects 13-17, further including a step of reading a cartridge ID on the housing.

18. A drug delivery device including: a reusable housing; a cassette coupled to the reusable housing, wherein the cassette has a ratio of height to diameter from 2:1 to 1:1; a cartridge supported by cassette and configured to retain a volume of a medication; and an orientation mechanism configured to orient the cassette relative to the reusable housing.

19. The drug delivery device of aspect 18, further including at least one motor supported by the reusable housing, wherein the orientation mechanism orients the cassette to operably couple the at least one motor with at least a portion of the cassette.

20. The drug delivery device of aspect 19, further including a needle assembly directly coupled to and at least partially within the cassette movable between an extended configuration and a retracted configuration, wherein in the extended configuration the needle assembly provides fluid communication between the polymeric cartridge and the needle assembly.

21. A drug delivery device including a cassette to couple to a reusable module, the cassette including: a cartridge configured to retain a volume of a medication, the cartridge extending between a proximal end and a distal end along an axis that is centrally located; a stopper driving system configured to drive the medication from the cartridge, the stopper driving system including a stopper and an interfacing end coupled to the stopper and configured to be driven by a first motor or actuating device of the reusable module to move the stopper; and a needle assembly directly coupled to the cartridge movable between an extended configuration and a retracted configuration, the needle assembly having an actuating gear movable between first and second positions, the actuating gear configured to be directly or indirectly driven by a second motor or actuating device of the reusable module, wherein in the extended configuration the actuating gear is in the second position and the needle assembly provides fluid communication between the cartridge and the needle assembly, wherein in the retracted configuration the actuating gear is in the first position and no fluid communication is provided between the cartridge and the needle assembly, wherein the interfacing end extends from an upper end of the cartridge and coaxial with the axis, and the actuating gear is disposed to be engaged externally by the second motor or actuating device of the reusable module at a location offset from the axis.

22. The drug delivery device of aspect 21, wherein the actuating gear further includes an external gear drivably engaged with the actuating gear, the external gear including external gear interface features disposed circumferentially spaced from one another around the axis, wherein the external gear interface features of the external gear configured to be driven by the second motor or actuating device of the reusable module.

23. The drug delivery device of aspect 22, wherein the external gear has a ring-shaped body, and the external gear interface features are disposed along a circumferential surface of the ring shaped body, and the external gear includes gear driving teeth formed along an axial edge of the ring shaped body for axial engagement with the actuating gear.

24. The drug delivery device of any one of aspects 21-24, wherein the actuating gear further includes an external gear drivably engaged with the actuating gear, the external gear including external gear interface features disposed circumferentially spaced from one another around the axis, wherein the external gear interface features of the external gear configured to be driven by the second motor or actuating device of the reusable module.

25. The drug delivery device of aspect 24, wherein the external gear has a ring-shaped body, and the external gear interface features are disposed along a circumferential surface of the ring shaped body, and the external gear includes gear driving teeth formed radially along an axial edge of the ring shaped body for radial engagement with the actuating gear.

26. The drug delivery device of any one of aspects 21-25, wherein the actuating gear has a rotating axis that is perpendicular to the axis.

What is claimed is:

1. A drug delivery device comprising a cassette to couple to a reusable module, wherein the cassette comprises:
    a cartridge configured to retain a volume of a medication, the cartridge extending between a proximal end and a distal end along an axis that is centrally located;
    a stopper driving system configured to drive the medication from the cartridge, the stopper driving system comprising a stopper and an interfacing end coupled to the stopper and configured to be driven by a first motor or a first actuating device of the reusable module to move the stopper; and
    a needle assembly directly coupled to the cartridge and movable between an extended configuration and a retracted configuration, the needle assembly having an actuating gear rotatable in a first direction and a second direction opposite the first direction, the actuating gear configured to be directly or indirectly driven by a second motor of the reusable module, wherein in the extended configuration after rotation of the actuating gear in the first direction the needle assembly is configured to provide fluid communication between the cartridge and the needle assembly, wherein in the retracted configuration after rotation of the actuating gear in the second direction no fluid communication is provided between the cartridge and the needle assembly, wherein the needle assembly is moved to the retracted configuration after being in the extended configuration,
    wherein the interfacing end extends from an upper end of the cartridge and coaxial with the axis, and the actuating gear is disposed at a location offset from the axis, and
    wherein the drug delivery device further comprises the reusable module, the reusable module comprising the first motor configured to actuate the stopper driving system to deliver the medication from the cartridge, and the second motor configured to actuate the actuating gear of the needle assembly.

2. The drug delivery device of claim 1, further comprising an external gear drivably engaged with the actuating gear, the external gear configured to be driven by the second motor of the reusable module.

3. The drug delivery device of claim 2, wherein the external gear has a ring-shaped body, the external gear including gear driving teeth disposed along a circumferential surface of the ring shaped body and formed along an axial edge of the ring shaped body for axial engagement with the actuating gear.

4. The drug delivery device of claim 1, wherein the actuating gear further comprises an external gear drivably engaged with the actuating gear, the external gear including external gear interface features disposed circumferentially spaced from one another along a radially facing surface around the axis, wherein the external gear interface features of the external gear configured to be driven by the second motor of the reusable module.

5. The drug delivery device of claim 4, wherein the external gear has a ring-shaped body, and the external gear interface features are disposed along a circumferential surface of the ring shaped body, and the external gear includes gear driving teeth formed radially along an axial edge of the ring shaped body for radial engagement with the actuating gear.

6. The drug delivery device of claim 1, wherein the actuating gear has a rotating axis that is perpendicular to the axis.

7. The drug delivery device of claim 1, wherein the cartridge includes a fluid housing comprising the medication.

8. The drug delivery device of claim 1, wherein the reusable module is configured to receive the cassette and comprises a driving system configured to operatively couple to at least the stopper driving system.

9. The drug delivery device of claim 8, further comprising an orientation mechanism configured to orient the cassette relative to the reusable module when the cassette is coupled to the reusable module.

10. The drug delivery device of claim 9, wherein the orientation mechanism comprises a protrusion and the reusable module comprises a slot configured to receive the protrusion.

11. The drug delivery device of claim 8, wherein the reusable module is configured to receive the cassette at any rotational position around said axis of the cassette.

12. The drug delivery device of claim 1, wherein the cassette has a height from 40 mm to 60 mm and a diameter from 20 mm to 40 mm.

13. The drug delivery device of claim 1, further comprising a cartridge ID coupled to the cartridge.

14. The drug delivery device of claim 13, wherein the cartridge ID comprises at least one circular ID, the circular ID configured to be read from a plurality of rotational orientations relative to a central axis of the circular ID.

15. The drug delivery device of claim 14, wherein the cartridge ID comprises at least one of an RFID indicator, a readable chip, and an antenna.

16. The drug delivery device of any one of claim 1, wherein the cartridge is composed of a polymer, or wherein at least one of the at least a portion of the stopper driving system and the needle assembly is composed of a polymer.

\* \* \* \* \*

UNITED STATES PATENT AND TRADEMARK OFFICE
CERTIFICATE OF CORRECTION

PATENT NO. : 12,239,816 B2
APPLICATION NO. : 18/246631
DATED : March 4, 2025
INVENTOR(S) : Murat Günay et al.

Page 1 of 1

It is certified that error appears in the above-identified patent and that said Letters Patent is hereby corrected as shown below:

In the Claims

In Claim 16, Column 24, Line 24 (approx.), after "of" delete "any one of".

Signed and Sealed this
Twenty-eighth Day of October, 2025

John A. Squires
*Director of the United States Patent and Trademark Office*